(12) United States Patent
Namiki et al.

(10) Patent No.: US 9,983,530 B2
(45) Date of Patent: May 29, 2018

(54) DETERMINATION APPARATUS FOR DETERMINING TYPE OF RECORDING MEDIUM AND IMAGE FORMING APPARATUS USING THE SAME

(71) Applicant: CANON KABUSHIKI KAISHA, Tokyo (JP)

(72) Inventors: Teruhiko Namiki, Mishima (JP); Tsutomu Ishida, Suntou-gun (JP); Masafumi Monde, Yokohama (JP); Takuya Shono, Suntou-gun (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 363 days.

(21) Appl. No.: 14/939,452

(22) Filed: Nov. 12, 2015

(65) Prior Publication Data

US 2016/0152052 A1 Jun. 2, 2016

(30) Foreign Application Priority Data

Nov. 27, 2014 (JP) ................. 2014-240367

(51) Int. Cl.
*G03G 15/00* (2006.01)
*B41J 11/00* (2006.01)
*G01N 21/55* (2014.01)
*G01N 29/11* (2006.01)
*G01N 29/44* (2006.01)

(52) U.S. Cl.
CPC ........ *G03G 15/5029* (2013.01); *B41J 11/009* (2013.01); *G01N 21/55* (2013.01);
(Continued)

(58) Field of Classification Search
CPC ....... G03G 15/5029; G03G 2215/00776; B41J 11/009; G01N 21/55; G01N 29/11;
(Continued)

(56) References Cited

U.S. PATENT DOCUMENTS 6,668,144 B2   12/2003  Maruyama
7,239,817 B2    7/2007  Kaneko et al.
(Continued)

FOREIGN PATENT DOCUMENTS

JP   2002-182518 A   6/2002
JP   2004-107030 A   4/2004
(Continued)

OTHER PUBLICATIONS

U.S. Appl. No. 14/847,256 filed by Tetsuya Yamamoto et al., on Sep. 8, 2015, Yamamoto et al. (U.S. Pat. No. 9,372,461 B2) Jun. 21, 2016.

*Primary Examiner* — Rodney Bonnette
(74) *Attorney, Agent, or Firm* — Fitzpatrick, Cella, Harper & Scinto

(57) ABSTRACT

An apparatus for determining a type of a recording medium is provided. A detection unit detects a characteristic value indicating a physical characteristic of a recording medium. A measurement unit measures a moisture content correlated with a moisture content of the recording medium. A determination unit determines the type of the recording medium based on the moisture content and the characteristic value. The determination unit may correct the characteristic value using the moisture content or correct a rule for determining the type of the recording medium using the moisture content unit, and determines the type of the recording medium in accordance with the corrected characteristic value or the corrected rule.

17 Claims, 13 Drawing Sheets

(52) U.S. Cl.
CPC ......... *G01N 29/11* (2013.01); *G01N 29/4427* (2013.01); *G01N 2201/1214* (2013.01); *G01N 2291/0237* (2013.01); *G01N 2291/048* (2013.01); *G03G 2215/00776* (2013.01)

(58) Field of Classification Search
CPC ....... G01N 29/4427; G01N 2201/1214; G01N 2291/0237; G01N 2291/048
See application file for complete search history.

(56) References Cited

U.S. PATENT DOCUMENTS

| | | | |
|---|---|---|---|
| 7,548,708 B2 | 6/2009 | Nagasaki et al. | |
| 2008/0181636 A1* | 7/2008 | Izumi | G03G 15/1605 399/44 |
| 2012/0098880 A1* | 4/2012 | Izumi | B41J 3/60 347/16 |
| 2013/0195534 A1* | 8/2013 | Oohara | G03G 15/6576 399/406 |
| 2014/0234002 A1* | 8/2014 | Oohara | G03G 15/5029 399/406 |
| 2015/0037053 A1 | 2/2015 | Ishida | |
| 2015/0309459 A1 | 10/2015 | Watanabe et al. | |

FOREIGN PATENT DOCUMENTS

| | | |
|---|---|---|
| JP | 2004-216883 A | 8/2004 |
| JP | 2009-042541 A | 2/2009 |
| JP | 2010-197535 A | 9/2010 |

* cited by examiner

(12) United States Patent

DETERMINATION APPARATUS FOR DETERMINING TYPE OF RECORDING MEDIUM AND IMAGE FORMING APPARATUS USING THE SAME

BACKGROUND OF THE INVENTION

Field of the Invention

The present invention relates to a determination apparatus for determining the type of a recording medium and an image forming apparatus using the same.

Description of the Related Art

In order for an image forming apparatus to properly adjust a usage amount of toner or ink or properly reproduce a gradation characteristic of an original image, image forming conditions need to be adjusted in accordance with characteristics (grammage, thickness, surface property and the like) of a recording medium. Japanese Patent Laid-Open No. 2004-107030 proposes detecting the grammage (weight per unit of area) of a recording medium using ultrasonic waves. Japanese Patent Laid-Open No. 2002-182518 proposes detecting a surface property of a recording medium using a CMOS sensor.

If the type of a recording medium is detected using inventions described in Japanese Patent Laid-Open No. 2004-107030 and Japanese Patent Laid-Open No. 2002-182518 and image forming conditions are adjusted in accordance with the detected type, the image forming apparatus will be able to achieve an image quality of a certain level. However, in the inventions described in Japanese Patent Laid-Open No. 2004-107030 and Japanese Patent Laid-Open No. 2002-182518, variations in a detection value due to the moisture content of a recording medium is not considered, and thus there is room for further improving detection accuracy for the type of a recording medium.

SUMMARY OF THE INVENTION

In view of this, the present invention improves detection accuracy for the type of recording medium.

The present invention provides an apparatus for determining a type of a recording medium, comprising the following elements. A detection unit is configured to detect a characteristic value indicating a physical characteristic of a recording medium. A measurement unit is configured to measure a moisture content correlated with a moisture content of the recording medium. A determination unit is configured to determine the type of the recording medium based on the moisture content measured by the measurement unit and the characteristic value detected by the detection unit. The determination unit is further configured to correct the characteristic value detected by the detection unit using the moisture content measured by the measurement unit or corrects a rule for determining the type of the recording medium using the moisture content measured by the measurement unit, and determine the type of the recording medium in accordance with the corrected characteristic value or the corrected rule.

The present invention further provides an image forming apparatus comprising the following elements. An image forming unit is configured to form an image on a recording medium. A detection unit is configured to detect a characteristic value indicating a physical characteristic of the recording medium. A measurement unit is configured to measure a moisture content correlated with a moisture content of the recording medium. A determination unit is configured to determine an image forming condition of the image forming unit based on the moisture content measured by the measurement unit and the characteristic value detected by the detection unit. The determination unit is further configured to correct the characteristic value detected by the detection unit using the moisture content measured by the measurement unit or corrects a rule for determining the image forming condition using the moisture content measured by the measurement unit, and determine the image forming condition in accordance with the corrected characteristic value or the corrected rule.

Further features of the present invention will become apparent from the following description of exemplary embodiments (with reference to the attached drawings).

DESCRIPTION OF THE EMBODIMENTS

Figure 1:
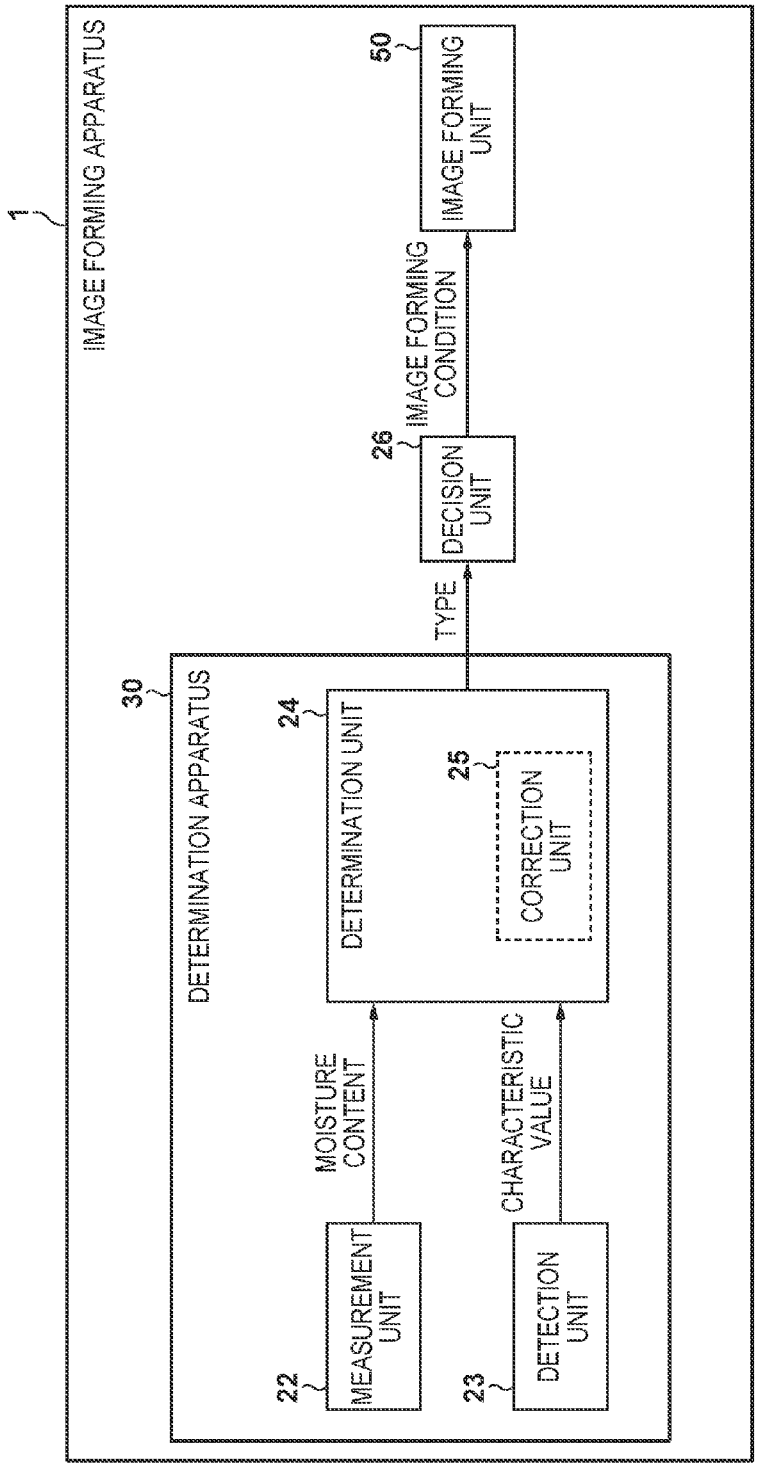
FIG. 1 is a block diagram showing functions of an image forming apparatus.

A technical idea of embodiments of the present invention will be described with reference to FIG. 1. In FIG. 1, an image forming apparatus 1 is provided with an image forming unit 50 for forming an image using ink or toner. A determination apparatus 30 determines the type of a recording medium on which an image is to be formed by the image forming unit 50. The type of a recording medium includes plain paper, thick paper, thin paper, coated paper, bond paper and the like. The determination apparatus 30 has a measurement unit 22 for measuring a moisture content correlated to a moisture content of a recording medium, a detection unit 23 for detecting a characteristic value indicating a physical characteristic of the recording medium, and a determination unit 24 for determining the type of the recording medium based on the moisture content and the characteristic value. The determination unit 24 may have a correction unit 25 for correcting a characteristic value and a rule for determining the type of the recording medium in accordance with a moisture content. The determination unit 24 determines the type of the recording medium in accordance with the characteristic value or the rule corrected by the correction unit 25. The physical characteristic of a recording medium includes the grammage and the surface property of the recording medium, for example, and is a parameter that influences image forming conditions. The grammage and the surface property of a recording medium change in accordance with the moisture content contained in the recording medium. Therefore, under an environment in which this moisture content deviates from a moisture content that was envisioned in advance, determination accuracy for the type of the recording medium can deteriorate. Therefore, in this embodiment, the correction unit 25 corrects a characteristic value output from the detection unit 23 and the rule for determining the type of the recording medium in accordance with the moisture content contained in the recording medium, thereby improving the determination accuracy for the type of the recording medium. The rule for determining the type of the recording medium is a rule for comparing one or more thresholds and the characteristic value and determining the type in accordance with the comparison result, for example. Therefore, correcting the rule includes correcting the threshold. By taking the moisture content of a recording medium into consideration in this manner, detection accuracy for the type of the recording medium improves. Note that the moisture content of the recording medium may be directly measured, but indirect measurement can make the configuration of the measurement unit 22 simpler. Commonly, the moisture content of a recording medium is correlated with the moisture content of the space around the recording medium. Therefore, it is sufficient that the measurement unit 22 measures the moisture content around the recording medium. However, unless the measurement unit 22 is separated from a heat source such as a fixing apparatus by a predetermined distance or more, the measurement unit 22 erroneously detects the moisture content due to the influence of the heat source. In particular, the measurement unit 22 that detects the temperature and the humidity and calculates a moisture content is likely to be influenced by a heat source. In the case where the measurement unit 22 cannot be arranged near the recording medium, the measurement unit 22 is at least arranged at a position away from a heat source. For example, the measurement unit 22 may be arranged on a conveyance path that is away from a main heat source by a predetermined distance or more, in a housing unit for accommodating a recording medium, or the like. It is not necessary for the measurement unit 22 to be mounted directly on the conveyance path or the housing unit, and it is sufficient that it is arranged around the conveyance path or the housing unit.

First Embodiment

The image forming apparatus 1 will be described with reference to FIG. 2. Here, an electrophotographic method is adopted as an image forming method of the image forming apparatus 1, but an electrostatic recording method, an ink jet recording method or the like may be adopted. Moreover, the image forming apparatus 1 is described as forming a multicolor image, but may be an image forming apparatus for forming a single-color image.

The image forming apparatus 1 is a tandem type color laser beam printer and outputs a multicolor image by superimposing images of a plurality of developing agents with different colors. The developing agents are four color toners, for example, yellow (Y), magenta (M), cyan (C), and black (K). A feeding cassette 2 is an example of a feeding unit and accommodates a recording medium P. A conveyance apparatus is provided on a conveyance path for the recording medium P. The conveyance apparatus is provided with a pair of conveyance rollers 5 and 6 for conveying the recording medium P fed from a feeding roller 4 for feeding the recording medium P from the feeding cassette 2, or from the feeding cassette 2. A photoreceptor drum 11 is an image carrier for carrying an electrostatic latent image and a toner image. A charging roller 12 is a charging unit for uniformly charging the surface of the photoreceptor drum 11 to a predetermined potential. A laser scanner 13 is an exposure apparatus or an optical scanning apparatus that irradiates the surface of the photoreceptor drum 11 with light in accordance with an image signal to form an electrostatic latent image. A process cartridge 14 has a developing roller 15. The developing roller 15 is a developing unit that develops an electrostatic latent image formed on the photoreceptor drum 11 using toner to visualize the image. A primary transfer roller 16 is a transfer unit for primarily transferring a toner image formed on the photoreceptor drum 11 to an intermediate transfer belt 17. The intermediate transfer belt 17 is an intermediate transfer member that is driven by a driving roller 18 and conveys a toner image transferred from the photoreceptor drum 11. A secondary transfer roller 19 is a transfer unit for transferring a toner image formed on the intermediate transfer belt 17 to the recording medium P. A fixing apparatus 20 is a unit for melting and fixing a toner image transferred to the recording medium P while conveying the recording medium P.

Arrangement and Configuration of Determination Apparatus

Figure 2:
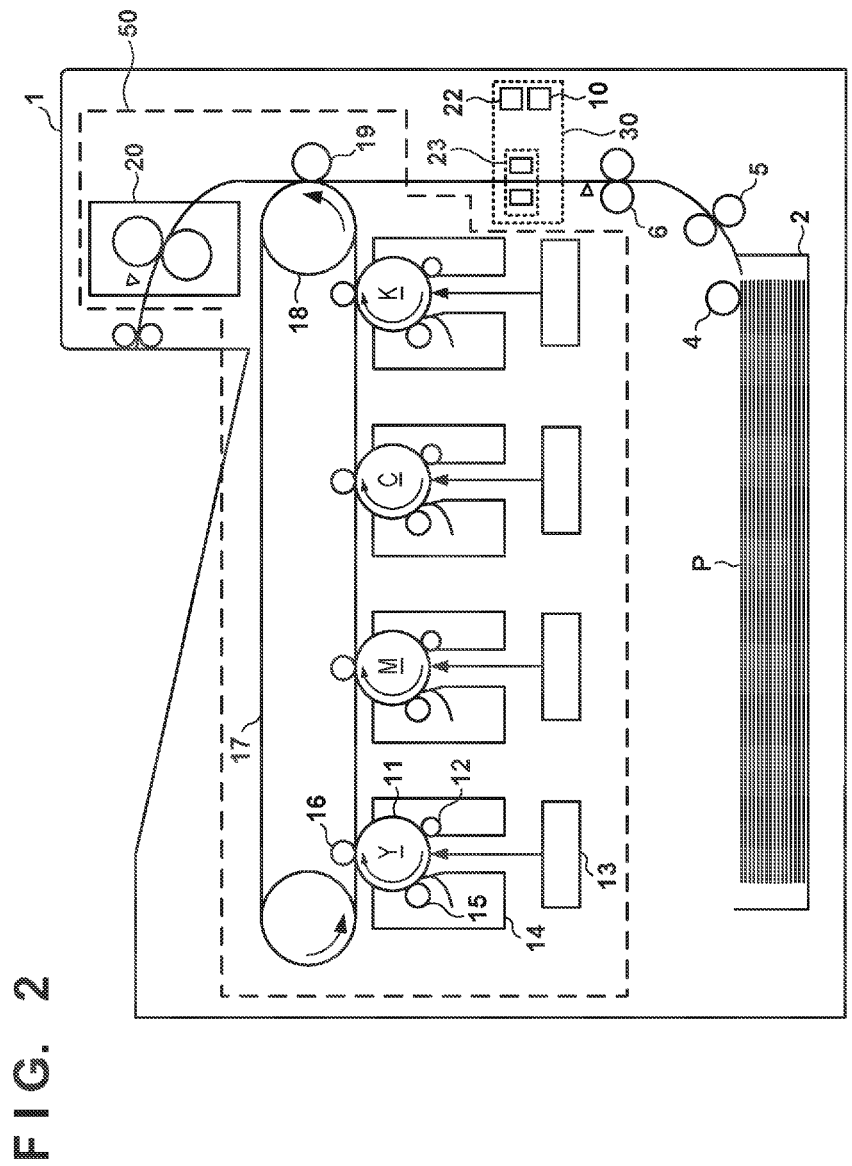
FIG. 2 is a diagram showing an example of a configuration of an image forming apparatus.

As shown in FIG. 2, the determination apparatus 30 is provided on the conveyance path for a recording medium P. The main heat source in the image forming apparatus 1 is the fixing apparatus 20, and the measurement unit 22 for measuring the moisture content is arranged at a position separated from the fixing apparatus 20. A control unit 10 functions as the above-described determination unit 24, and also functions as a decision unit 26. Moreover, the control unit 10 may be provided with a calculation function, a signal processing function and the like of the measurement unit 22 and the detection unit 23.

Figure 3:
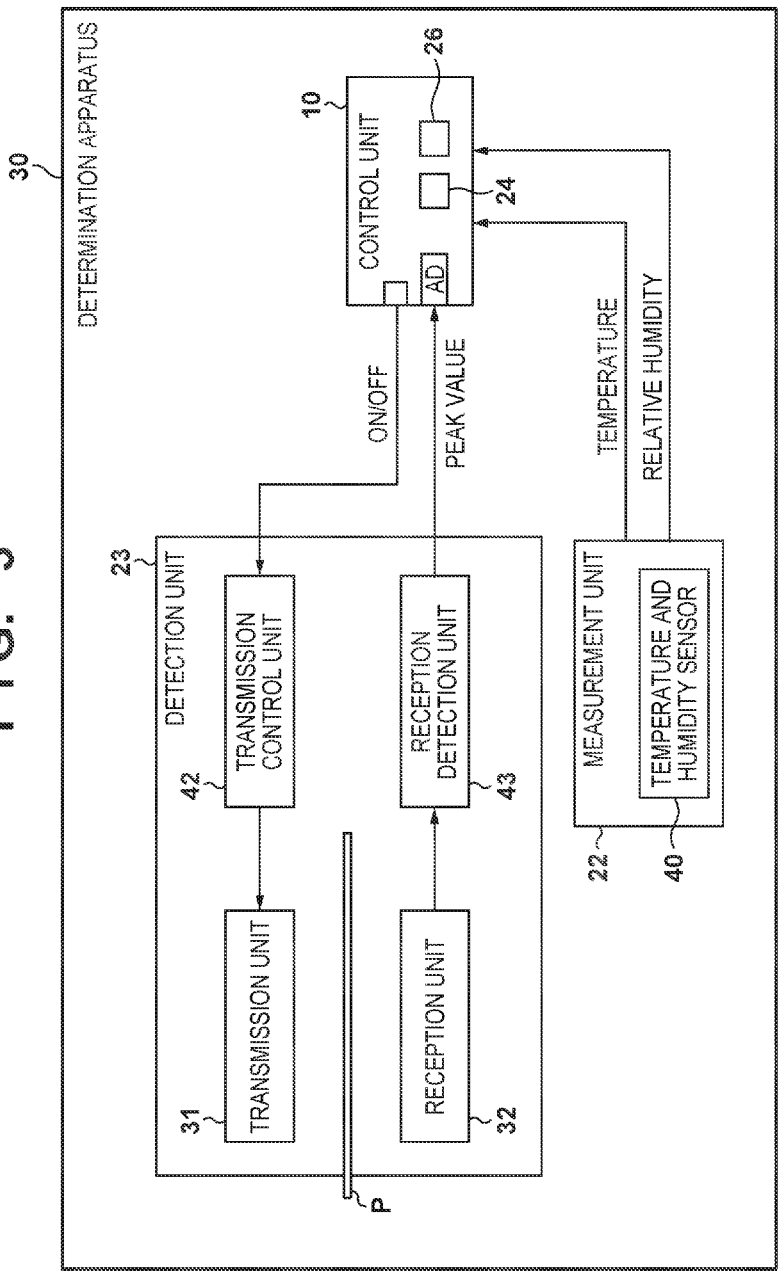
FIG. 3 is a block diagram showing functions of a determination apparatus.

The determination apparatus 30 for detecting the grammage of the recording medium P and determining the type of the recording medium P will be described with reference to FIG. 3. In this embodiment, as a method for determining the grammage, a method is adopted in which the recording medium P is irradiated with ultrasonic waves, the ultrasonic waves transmitted through the recording medium P are received, and a type is determined based on the amplitude of the reception signal.

The detection unit 23 functions as a grammage detection unit for detecting the grammage of the recording medium P conveyed thereto. The detection unit 23 has a transmission unit 31 and a reception unit 32. For example, the control unit 10 is constituted by an MPU (not illustrated) provided with a CPU, a memory, and the like, and executes control of the detection unit 23 and calculation processing for a measurement result of the measurement unit 22. Moreover, the control unit 10 integrally controls the units of the image forming apparatus 1.

The measurement unit 22 detects a temperature and a relative humidity as parameters indicating a moisture content using a temperature and humidity sensor 40, and outputs the temperature and the relative humidity to the control unit 10. The control unit 10 determines an image forming condition (print mode) in accordance with the type of the recording medium P, based on a measurement result of the measurement unit 22 and a detection value of the detection unit 23. The control unit 10 performs collective control of an electrophotographic process in addition to control of the detection unit 23 and the measurement unit 22 and processing of a detection result, but an independent control unit may be provided for these processes. For example, a first control unit for performing control of the detection unit 23 and the measurement unit 22 and processing of a detection result, and a second control unit for performing control of the electrophotographic process may be provided so that the first control unit and the second control unit communicate to share information. Moreover, a first control unit for performing control of the detection unit 23 and a second control unit for performing processing of a measurement result of the measurement unit 22 and control of the electrophotographic process may be provided such that the first control unit and the second control unit communicate to share information.

The measurement unit 22 detects a temperature and a humidity using the temperature and humidity sensor 40, so as to indirectly measure a moisture content. In this embodiment, the temperature and humidity sensor 40 is used, but a sensor other than the temperature and humidity sensor 40 may be used as long as the sensor is an environment sensor capable of detecting an environment parameter that enables a moisture content to be obtained. The temperature and humidity sensor 40 is arranged in a place that is near the exterior of the image forming apparatus 1 and is unlikely to be influenced by a heat source in the image forming apparatus 1 so that the temperature and the humidity near the image forming apparatus 1 can be detected. However, it is sufficient that the temperature and the humidity near the image forming apparatus 1 can be detected, and therefore the arrangement place is not limited thereto. The measurement unit 22 may obtain the moisture content near the image forming apparatus 1 from a detection result of the temperature and humidity sensor 40 using a conversion table or a function set based on correlation data between the temperature and the humidity near the image forming apparatus 1 and the detection result of the temperature and humidity sensor 40 in the image forming apparatus 1. Note that a conversion function (from the temperature and the humidity) into a moisture content may be provided in the measurement unit 22 or in the control unit 10.

The detection unit 23 has the transmission unit 31 for transmitting ultrasonic waves and the reception unit 32 for receiving ultrasonic waves. When the recording medium P is conveyed between the transmission unit 31 and the reception unit 32, the control unit 10 instructs a transmission control unit 42 to perform an operation start. Upon receiving the instruction of the operation start, the transmission control unit 42 generates a drive signal for transmitting ultrasonic waves of a specific frequency and supplies the drive signal to the transmission unit 31. The transmission unit 31 is driven by the drive signal, generates ultrasonic waves of a specific frequency, and transmits the ultrasonic waves toward the recording medium P. The reception unit 32 receives the ultrasonic waves transmitted through the recording medium P and outputs a reception signal. A reception detection unit 43 outputs the peak value of the amplitude of the reception signal as a detection voltage to an AD port of the control unit 10. The control unit 10 receives the output from the reception detection unit 43 using the AD port. The AD port of the control unit 10 converts the detection voltage into a digital detection value (dec value) (both the analog detection voltage and the digital detection value are parameters correlated with a characteristic value). For example, the AD port generates a dec value with a resolution of 256 levels based on a power supply voltage input to the control unit 10. More specifically, the AD port converts the detection voltage into the dec value so as to indicate the proportion of the input detection voltage with respect to the resolution. For example, if the power supply voltage of the control unit 10 is 3.3 V and the detection voltage input to the AD port is 1.65 V, the AD port outputs 128 as the dec value. In this embodiment, the dec value was described as being expressed in 256 levels, but this resolution is merely an example.

Upon receiving a detection voltage (when generating a dec value), the control unit 10 instructs an operation stop of the transmission control unit 42. The transmission control unit 42 stops generation of the drive signal in accordance with the instruction of the operation stop. This stops transmission of ultrasonic waves. A sheet sensor may be used. The control unit 10 causes ultrasonic waves to be transmitted when a sheet is passing by the detection unit 23, and stops transmission of ultrasonic waves when a sheet is not passing by the detection unit 23. This makes it possible to achieve power consumption reduction and noise reduction.

The attenuation amount of ultrasonic waves transmitted through the recording medium P is proportional to the grammage of the recording medium P. That is, the larger the grammage of the recording medium P is, the larger the attenuation amount of ultrasonic waves is. In the case of a recording medium P with a small grammage (thin paper), the attenuation amount of ultrasonic waves is small, and the peak value of the reception signal and the dec value are large. Conversely, in the case of a recording medium P with a large grammage (thick paper), the attenuation amount of ultrasonic waves is large, and the peak value and the dec value are small. For example, in the case where the dec value is large, the determination unit 24 determines that the type of the recording medium P is thin paper. Moreover, in the case where the dec value is small, the determination unit 24 determines that the type of the recording medium P is thick paper. Commonly, the grammage of plain paper is less than or equal to 115 $g/m^2$, while the grammage of coated paper exceeds 115 $g/m^2$. For example, assume that the dec value obtained by the detection unit 23 detecting a recording medium P having a grammage of 115 $g/m^2$ is 90 dec. In this case, the determination unit 24 sets 90 dec as a first threshold, and if the dec value exceeds the first threshold, determines that the recording medium P is plain paper. Moreover, if the dec value is less than or equal to the first threshold, the determination unit 24 may determine that the recording medium P is coated paper. As an example, the type threshold is set to 90 dec, but the type threshold can be freely set in accordance with the type that is desired to be determined. In general, the grammage of thin paper is often less than or equal to 70 $g/m^2$. Assume that the dec value obtained by the detection unit 23 detecting a recording medium P with a grammage of 70 $g/m^2$ is 150 dec. In this case, the determination unit 24 sets 150 dec as a second threshold, and if the dec value exceeds the second threshold, determines that the recording medium P is thin paper. Moreover, if the dec value is less than or equal to the second threshold and exceeds the first threshold, the determination unit 24 may determine that the recording medium P is plain paper. In this manner, with a plurality of type thresholds, determination of three types or more is possible.

Type of Recording Medium and Image Forming Condition

In general, the electrical resistance value of the recording medium P is different depending on the grammage of the recording medium P, and therefore the decision unit 26 of the control unit 10 adjusts transfer conditions such as the transfer current and the transfer voltage necessary for transferring toner. Moreover, the thermal capacity is different in accordance with the grammage of the recording medium P, and therefore the decision unit 26 adjusts fixing conditions such as the fixing temperature and the fixing time for fixing toner and the conveyance speed of the recording medium P. The amount of heat that propagates to the toner and the recording medium P changes due to adjusting these fixing conditions. Therefore, the decision unit 26 sets image forming conditions (the transfer conditions, the fixing conditions, and the like) applied to the image forming unit 50 in accordance with the type of the recording medium P.

Moisture Content and Image Forming Conditions

The resistance value and the grammage of the recording medium P change in accordance with the moisture content. Therefore, the decision unit 26 sets the image forming conditions in accordance with the resistance value and the grammage of the recording medium P in consideration of the moisture content. The change in the resistance value of the recording medium P in accordance with the moisture content differs depending on the type of the recording medium P. That is, the decision unit 26 sets the image forming conditions in accordance with the type and the moisture content of the recording medium P, so that a desired image quality is achieved.

Influence of Moisture Content on Determination of Type of Recording Medium

The influence that the moisture content has on determination of the type of the recording medium P will be described. The grammage of the recording medium P changes due to the moisture content near the recording medium P. For example, if the moisture content is large, the moisture content contained in fibers composing the recording medium P increases, and thus the grammage of the recording medium P increases due to the contained moisture content. On the other hand, if the moisture content is small, the moisture content contained in fibers composing the recording medium P decreases and thus the grammage decreases. Therefore, the moisture content near the recording medium P influences determination of the type of the recording medium P. For example, the determination result of the recording medium P is sometimes different between the case where the type of the recording medium P is determined based on the dec value of the grammage that has changed due to the moisture content and the case where the type of the recording medium P is determined after the dec value of the grammage is converted into a dec value under an environment with a specific moisture content. In view of this, the correction unit 25 converts the dec value of the grammage into a dec value in a specific environment and subsequently the determination unit 24 determines the type of the recording medium P so that desired detection accuracy is achieved.

In this embodiment, as an example of the moisture content, an absolute moisture content obtained based on the temperature and the humidity is used. The correction unit 25 executes conversion processing of the dec value based on an environment in which the absolute moisture content is approximately 11.5 g/m³ (corresponding to a temperature of 25 C and a humidity of 50% RH). In this embodiment, the absolute moisture content is used as an example, but it is sufficient that the moisture content that is correlated with the moisture content contained in the recording medium P is used, and the moisture content other than the absolute moisture content, for example, a moisture content obtained based on a relative humidity may be used. For example, in the case of determining the type of the recording medium P within a temperature range in which change in moisture content is small, the moisture content contained in the recording medium P may be estimated based on the relative humidity near the recording medium P. In such a case, the moisture content obtained based on the relative humidity has accuracy similar to that of an absolute moisture content obtained based on the temperature and the humidity.

Relation Between Moisture Content and Detection Result

Figure 4:
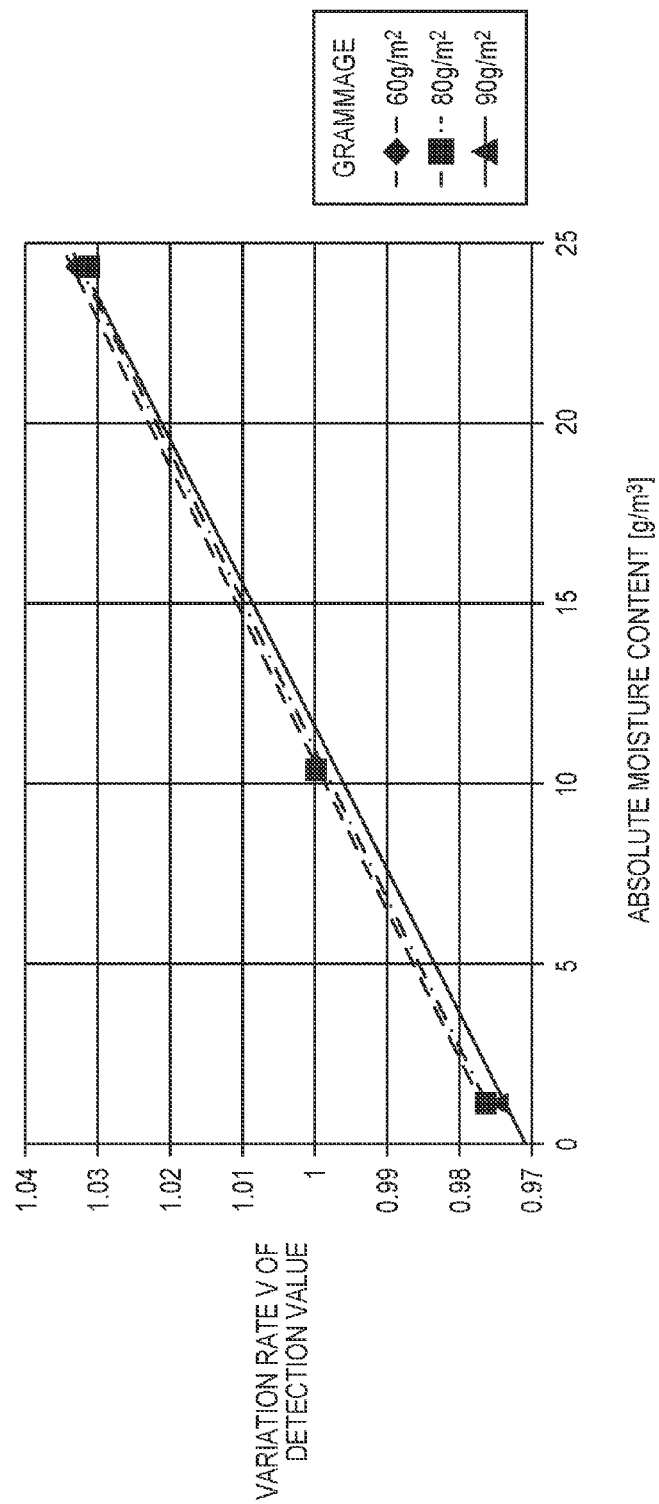
FIG. 4 is a diagram showing an example of a variation rate of a moisture content and a characteristic value.

Next, influence that variation in moisture content detected based on the detection result of the temperature and humidity sensor 40 has on the detection value of the detection unit 23 will be described with reference to inventors' experiment results shown in FIG. 4. As described above, in this embodiment, the absolute moisture content around the recording medium P is used in order to estimate the moisture content contained in the recording medium P. In FIG. 4, the horizontal axis indicates the absolute moisture content detected by the temperature and humidity sensor 40. The vertical axis indicates the variation rate V of the dec value based on the dec value in an environment where the absolute moisture content is approximately 11.5 g/m³ (corresponding to a temperature of 25 C and a humidity of 50% RH). Here, as an example, variation rates V for recording media P (plain paper) having grammages of 60 g/m², 80 g/m², and 90 g/m² are shown. Measurement is executed after each of the recording media P is sufficiently adapted to the temperature and humidity environment.

Because the grammage increases/decreases in accordance with increase/decrease in moisture content, the relation between the absolute moisture content and the variation rate V of the dec value is linear as shown in FIG. 4. That is, it can be seen that the dec value of the recording medium P changes in proportion to the moisture content near the recording medium P. Therefore, by substituting the moisture content in an approximation equation of the variation rate V obtained from FIG. 4, the variation rate V of the dec value is determined. The correction unit 25 then corrects or converts the dec value into a dec value under a specific environment by dividing the dec value by the variation rate V.

corrected dec value=
    dec value/variation rate $V$     Correction Equation1

As an example, as shown in FIG. 4, the dec value of the recording medium P of grammage 60 g/m² under an environment in which the absolute moisture content is 20 g/m³ is 1.022 times the dec value under an environment in which the absolute moisture content is 11.5 g/m³. Therefore, the correction unit 25 divides the dec value by 1.022 in order to convert the dec value into the dec value under the specific environment in which the absolute moisture content is 11.5 g/m³. That is, the correction unit 25 divides the dec value by the variation rate V, so that the dec value is corrected to a dec value under a specific environment.

As for the three types of the recording media P (plain paper) shown in FIG. 4, it can be seen that variation in the variation rate V is small regardless of the difference in grammage. Therefore, as for a plurality of recording media P with small differences in grammage, the dec value can be accurately corrected even if the approximation equation is not changed in accordance with the type of the recording medium P. In the case of this embodiment, the correction unit 25 obtains the variation rate V of the dec value of the detection unit 23 by substituting the moisture content obtained by the temperature and humidity sensor 40 in the following approximation equation 1. As described above, the coefficient of the approximation equation 1 is determined based on the variation rate V of the dec value for the absolute moisture content of the recording medium P having the grammage of 80 g/m² in FIG. 4.

variation rate $V=0.03\times$ moisture content(g/m²)+0.98    Approximation equation 1

Here, the approximation equation 1 of the variation rate V is an example in this embodiment, and is appropriately set in accordance with the detection characteristics of the detection unit 23. Moreover, in this embodiment, the dec value is corrected based on the moisture content obtained from the detection result of the temperature and humidity sensor 40. However, it is sufficient that the determination result for the type of the recording medium P that is in accordance with the moisture content can be obtained, and the present invention is not limited only to a method in which the dec value is corrected. For example, the target of correction does not need to be the dec value, and the rule that is used for determining the type of the recording medium P, that is, the type threshold for the dec value may be changed. For example, the correction unit 25 may increase/decrease 90 dec, which is the type threshold for distinguishing between plain paper and coated paper, in accordance with the moisture content. Accordingly, detection accuracy for the type of the recording medium P that is in accordance with the moisture content improves without correcting the dec value. Alternatively, a method other than the method in which the dec value or the type threshold is corrected may be adopted. For example, the determination unit 24 may store, in a storage unit, a table indicating the relation between the moisture content near the recording medium P and the dec value, and refer to the table based on the obtained moisture content and dec value and identify the type of the recording medium P. For example, a table, based on which it is determined that the type of the recording medium P is plain paper in the case where the moisture content is 11.5 g/m³ and the dec value corresponds to a grammage of 116 g/m² and it is determined that the type of the recording medium P is coated paper in the case where the moisture content is 5 g/m³ and the dec value corresponding to a grammage of 116 g/m², may be used. Moreover, the control unit 10 may control image forming conditions of the image forming apparatus 1 directly based on the corrected dec value without determining the type of the recording medium P. Alternatively, the image forming conditions of the image forming apparatus 1 may be controlled directly based on the dec value and the corrected rule. For example, the correspondence relation between the dec value or the like and an image forming condition is stored in advance in a storage apparatus, so that an image forming condition is determined directly based on the dec value or the like.

In this embodiment, the moisture content near the recording medium P is handled as the same as the moisture content near the image forming apparatus 1. In general, the recording medium P is placed in the feeding cassette 2, a feeding tray, or an optional feeder. That is, the recording medium P is located in a place which is not significantly influenced by a power supply apparatus within the image forming apparatus 1 or a heat source such as a driving source. Therefore, the moisture content near the recording medium P is considered substantially the same as the moisture content near the image forming apparatus 1. In this embodiment, the moisture content near the recording medium P was obtained using the temperature and humidity sensor 40 for detecting the moisture content near the image forming apparatus 1. However, it is sufficient that the moisture content near the recording medium P can be obtained, and the method for obtaining the moisture content is not limited thereto. For example, the dedicated temperature and humidity sensor 40 may be arranged in the feeding cassette 2.

Flowchart

Figure 5:
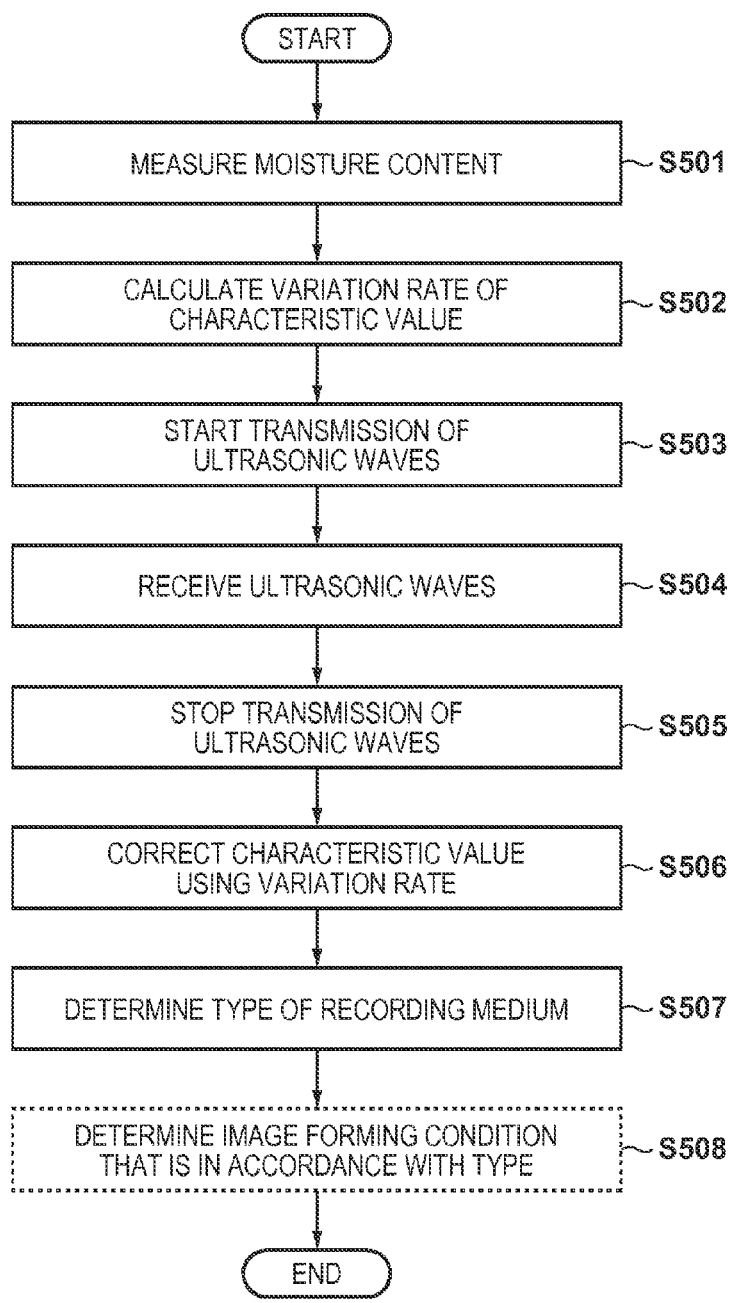
FIG. 5 is a flowchart showing a recording medium determination method.

A method for determining the type of the recording medium P in the control unit 10 will be described with reference to FIG. 5. In step S501, the control unit 10 (the measurement unit 22 or the determination unit 24) measures the moisture content related to the recording medium P using the temperature and humidity sensor 40. For example, the control unit 10 obtains a measurement value of the temperature and a measurement value of the humidity from the temperature and humidity sensor 40, and converts the measurement value of the temperature and the measurement value of the humidity into an absolute moisture content using a function or a table.

In step S502, the control unit 10 (the determination unit 24 and the correction unit 25) calculates the variation rate V which is a correction coefficient for correcting a characteristic value (e.g., grammage). For example, the control unit 10 may calculate the variation rate V by substituting the moisture content in the above-described approximation equation 1.

In step S503, the control unit 10 starts transmission of ultrasonic waves. As described above, the control unit 10 instructs the transmission control unit 42 to start transmission of ultrasonic waves. This may involve sending out an ON signal to the transmission control unit 42, for example. Note that transmission and stopping of ultrasonic waves may be controlled by supplying or cutting off operation electrical power for the transmission control unit 42 from a power supply.

In step S504, the control unit 10 executes ultrasonic wave reception processing. For example, the ultrasonic waves transmitted through the recording medium P are received by the reception unit 32, and a detection voltage is generated by the reception detection unit 43 and is input to the AD port of the control unit 10. The control unit 10 obtains the dec value, which is a characteristic value, by converting the analog detection voltage into a digital dec value.

In step S505, the control unit 10 stops the transmission of ultrasonic waves. The control unit 10 instructs the transmission control unit 42 to stop the transmission of ultrasonic waves as described above. This may involve sending out an OFF signal to the transmission control unit 42 or stopping the sending out of an ON signal, for example.

In step S506, the control unit 10 (the correction unit 25) corrects the characteristic value. For example, the correction unit 25 corrects the dec value, which is a characteristic value, based on the variation rate V. Correction may be performed using a function, a table, or the like in which the variation rate V and the characteristic value serve as inputs, and the corrected characteristic value serves as the output. For example, the function may be a function that is used for outputting a corrected characteristic value by dividing the dec value, which is a characteristic value, by the variation rate V.

In step S507, the control unit 10 (the determination unit 24) determines the type of the recording medium using the corrected characteristic value. For example, the determination unit 24 compares the characteristic value and one or more thresholds, and determines the type of the recording medium. A plurality of thresholds are used in order to determine three types or more.

In step S508, the control unit 10 (the decision unit 26) determines an image forming condition (e.g., transfer condition or fixing condition) that is in accordance with the type of the recording medium. Image forming conditions that are in accordance with types of recording media may be prepared in advance, and the decision unit 26 may select an image forming condition that is in accordance with the type of the recording medium from among the plurality of image forming conditions. Moreover, the decision unit 26 may also set image forming conditions in accordance with the type of recording medium and the moisture content. For example, the decision unit 26 may determine an image forming condition that is in accordance with the type of the recording medium and the moisture content by inputting the moisture content to a function or a table for obtaining an image forming condition prepared for each type of recording medium.

According to this embodiment, the determination apparatus 30 corrects a characteristic value of a recording medium P (e.g., detection value of grammage) based on a moisture content obtained from the temperature and humidity sensor 40, thereby improving detection accuracy for the type of the recording medium P. For example, it is possible to determine types of recording media P having a grammage difference of approximately 10 g/m² or less, for example, recording media P of grammages of 70 g/m² and 80 g/m², which could not be clearly determined conventionally due to variation caused by a moisture content. As a result, the apparatus 1 provided with the determination apparatus 30 can appropriately set an image forming condition in accordance with the determined type of the recording medium P, and thus image quality can be improved. Furthermore, as an example of a method for obtaining an appropriate image forming condition, the relation between an image forming condition and a combination of a moisture content and a detection value is stored in the control unit 10. Furthermore, it is also possible to determine an image forming condition without determining the type of the recording medium P, by referring to the relation based on a combination of an obtained moisture content and detection value. Such a relation may be tabulated.

Second Embodiment

In the first embodiment, the variation rate V of the grammage of a recording medium P is obtained based on a moisture content obtained from the temperature and humidity sensor 40, and a detection value is corrected based on the variation rate V. Note that the variation rate V of the first embodiment is obtained in the same manner regardless of the type of the recording medium P, thereby simplifying the calculation. In this embodiment, a method for determining a plurality of variation rates V is prepared in advance so as to improve detection accuracy for a specific type of a recording medium P such as coated paper. In a second embodiment, descriptions of portions common with those in the first embodiment are omitted for simplifying the description.

The type of the recording medium P used in the image forming apparatus 1 is not limited only to a general recording medium P (plain paper) composed of pulp fibers, and a recording medium P whose surface has a pigment applied thereto and has been subjected to smoothing processing (coated paper) is used in some cases. In particular, coated paper makes it possible to form a brightly colored image in multicolor printing, and opportunities for use have been increasing. If detection accuracy for a specific type of a recording medium P such as the above-described coated paper can be improved, a more appropriate image forming condition will be determined. In view of this, in this embodiment, correction of a characteristic value in the case where the recording medium P is coated paper will be described as an example. Note that the specific type of the recording medium P is not limited to coated paper, and it is also possible to correct a characteristic value for thin paper as an example.

Relation Between Type of Recording Medium P and Detection Value of Grammage

The influence on the detection value of the grammage in the case of different types of recording media P will be described with reference to FIG. 6. As described above, coated paper has a pigment applied to the surface thereof. Therefore, the grammage of the recording medium P will take a value that includes the grammage of the pigment. Moreover, the moisture absorptivity is significantly different between a pigment and a pulp material. A pigment has a low moisture absorptivity compared with a pulp material. Therefore, the variation rate V for coated paper is different from that for plain paper.

Figure 6:
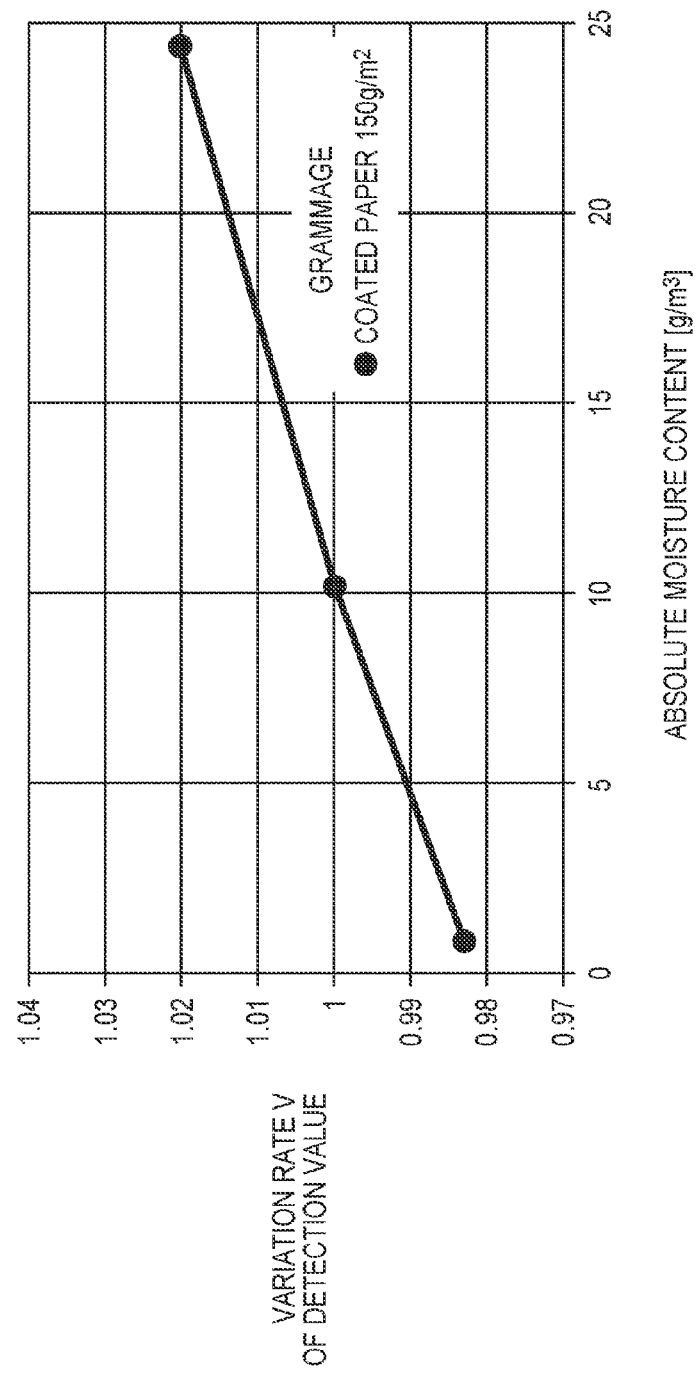
FIG. 6 is a diagram showing an example of a variation rate of a moisture content and a characteristic value.

In FIG. 6, the horizontal axis indicates the absolute moisture content measured using the temperature and humidity sensor 40. The vertical axis indicates the variation rate V obtained based on the grammage when the absolute moisture content is approximately 11.5 g/m³ (corresponding to a temperature of 25 C and a humidity of 50% RH). Here, the variation rate V for coated paper of 150 g/m² is shown as an example. Unlike the variation rate V for plain paper shown in FIG. 4, the variation rate V for coated paper shown in FIG. 6 has a narrow width over which the variation rate V varies and has a moderate slope. Similarly to the first embodiment, it is possible to determine an approximation equation 2 for obtaining the variation rate V for coated paper from FIG. 6.

$$\text{variation rate } V = 0.01 \times \text{moisture content g/m}^3 + 0.99 \quad \text{Approximation Equation 2}$$

Note that hereinafter, the variation rate obtained from the approximation equation 1 is denoted by V1 and the variation rate obtained from the approximation equation 2 is denoted by V2 in order to distinguish them.

Flowchart

Figure 7:
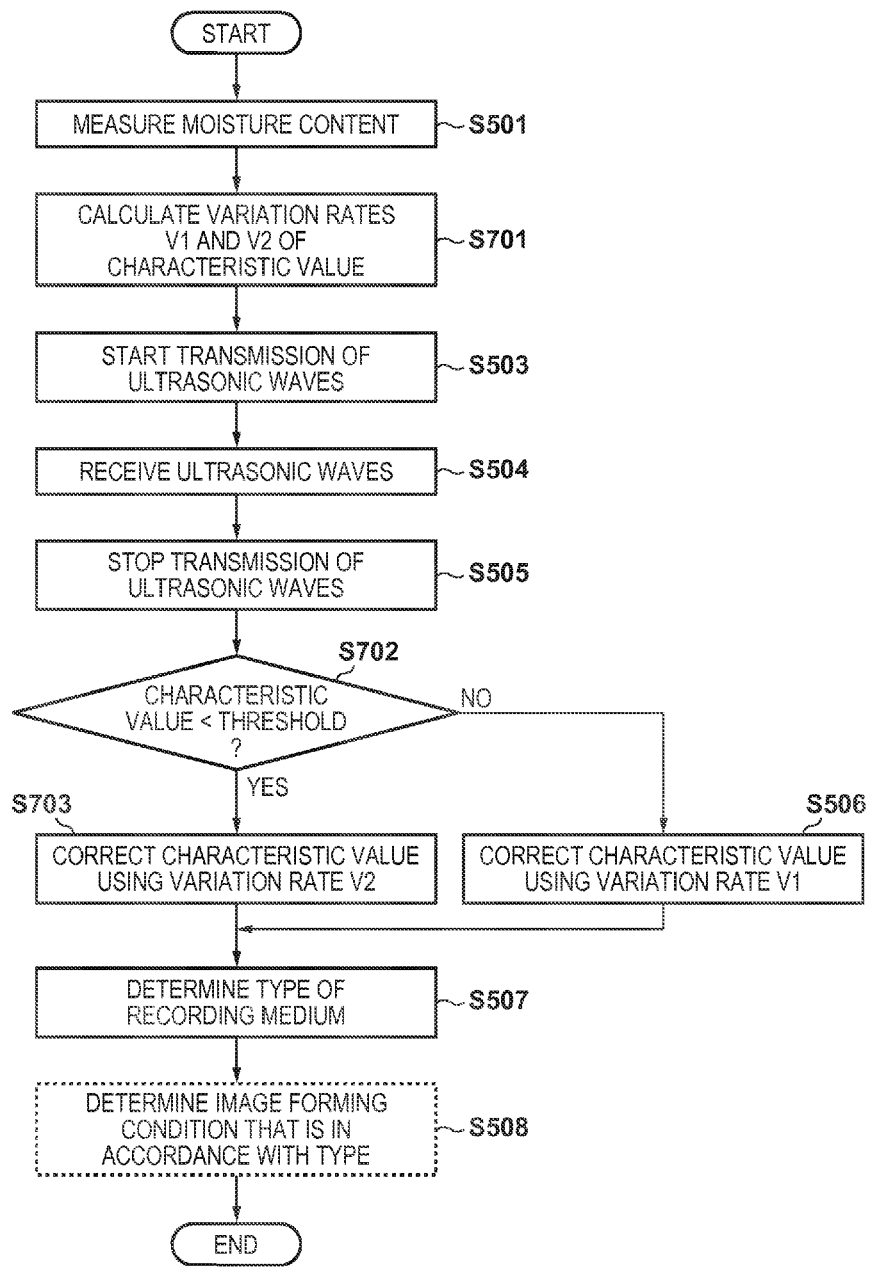
FIG. 7 is a flowchart showing a recording medium determination method.

A method for determining the type of the recording medium P in the control unit 10 will be described with reference to FIG. 7. Note that in FIG. 7, descriptions of steps that are the same as steps described with reference to FIG. 5 are omitted for simplification. Note that in FIG. 7, step S502 is replaced by step S701, and steps S702 and S703 are added after step S505.

In step S701, the control unit 10 (the determination unit 24 and the correction unit 25) calculates the variation rates V1 and V2, which are correction coefficients for correcting a characteristic value (e.g., grammage). For example, the control unit 10 may calculate the variation rates V1 and V2 by substituting the moisture content in the above-described approximation equation 1 and approximation equation 2. Subsequently, steps S503 to S505 are executed, and the procedure advances step S702.

In step S702, the control unit 10 (the determination unit 24) compares the dec value, which is a characteristic value, and a predetermined switching threshold, and determines whether or not the dec value is smaller than the predetermined switching threshold. The switching threshold is determined as follows, for example. In the second embodiment as well, similarly to the first embodiment, a grammage of 115 g/m² and 90 dec are in a corresponding relation. If the dec value is greater than or equal to 90 dec, the grammage is less than or equal to 115 g/m², and there is a high possibility that the recording medium P is plain paper. On the other hand, if the dec value is less than 90 dec, the grammage is greater than or equal to 115 g/m², and there is a high possibility that the recording medium P is coated paper. Note that the switching threshold (selection threshold for an approximation equation) is set to 90 dec, but this is merely an example. It is sufficient that the switching threshold is appropriately set in accordance with the type of the recording medium P that is to be determined with priority in the image forming apparatus 1. For example, in the case where it is desired to give priority to detection accuracy for coated paper, the switching threshold may be set to 95 dec in order to more appropriately correct a characteristic value for coated paper. In this manner, 5 dec may be added as a margin in order to give priority to coated paper. Accordingly, the number of types of recording media P determined to be coated paper will increase, and the number of cases where coated paper is not determined to be coated paper decreases.

If it is determined in step S702 that the dec value is smaller than the predetermined switching threshold, there is a high possibility that the type of the recording medium P is coated paper, and thus the procedure advances to step S703. In step S703, the correction unit 25 corrects the dec value, which is a characteristic value, using the variation rate V2 for coated paper. On the other hand, if it is determined in step S702 that the dec value is greater than or equal to the predetermined switching threshold, there is a high possibility that the type of the recording medium P is not coated paper, and thus the procedure advances to the above-described step S506. In step S506, the correction unit 25 corrects the dec value, which is a characteristic value, using the variation rate V1 for plain paper.

In this manner, the correction unit 25 selects the variation rate V1 or V2 depending on the dec value, which is synonymous with selecting an approximation equation. Accordingly, a characteristic value can be appropriately corrected depending on the dec value obtained from the recording medium P, and thereby the determination result for the type of the recording medium P will improve.

In this embodiment, plain paper and coated paper are described as examples of the type of the recording medium P, but the technical idea of the second embodiment is also applicable to any type of recording medium P. That is, the grammage of a recording medium P that has changed due to the moisture content near the recording medium P is measured in advance, and an approximation equation is obtained and stored in the control unit 10. Furthermore, a switching threshold is set based on the grammage of the recording medium P. This allows an appropriate approximation equation to be selected in accordance with the type of the recording medium P, and thus detection accuracy for the recording medium P will improve. The control unit 10 may be provided with an approximation equation for the dec value in the case of thin paper whose grammage is less than or equal to 70 g/m$^2$, as an example. If the dec value is greater than or equal to 150 dec, there is a high possibility that the type of the recording medium P is thin paper. Therefore, the correction unit 25 corrects the dec value using the approximation equation for the dec value corresponding to thin paper so that thin paper can be accurately determined.

In this manner, according to the second embodiment, an effect such as the following will be obtained in addition to the effect of the first embodiment. The determination apparatus 30 selects an approximation equation for the variation rate V in accordance with the type of the recording medium P (dec value). Thereby, detection accuracy for the recording medium P improves. For example, detection accuracy for the recording medium P can be improved for coated paper and thin paper similarly to plain paper. Additionally, the image forming apparatus 1 provided with the determination apparatus 30 sets an image forming condition in accordance with the determined type of the recording medium P, thereby achieving improvement in image quality. Here, description was given regarding selecting the variation rate V1 or V2 and selecting the approximation equation 1 or 2, which is equivalent to selecting or correcting a rule for determining a recording medium. Moreover, in the first and second embodiments, a characteristic value is corrected based on a variation rate, but the threshold used in the step of determining the type of the recording medium executed in step S507 may be corrected or selected based on the variation rate.

As described in the first embodiment, in the second embodiment as well, the control unit 10 may control image forming conditions of the image forming apparatus 1 directly based on the corrected dec value without determining the type of the recording medium P. Alternatively, image forming conditions of the image forming apparatus 1 may be controlled directly based on the dec value and the corrected rule.

Third Embodiment

In the first and second embodiments, the type of the recording medium P is determined using ultrasonic waves, but another method may be used. A method for determining the type of the recording medium P by irradiating the recording medium P with light and detecting reflection light from the recording medium P will be described below.

Figure 8:
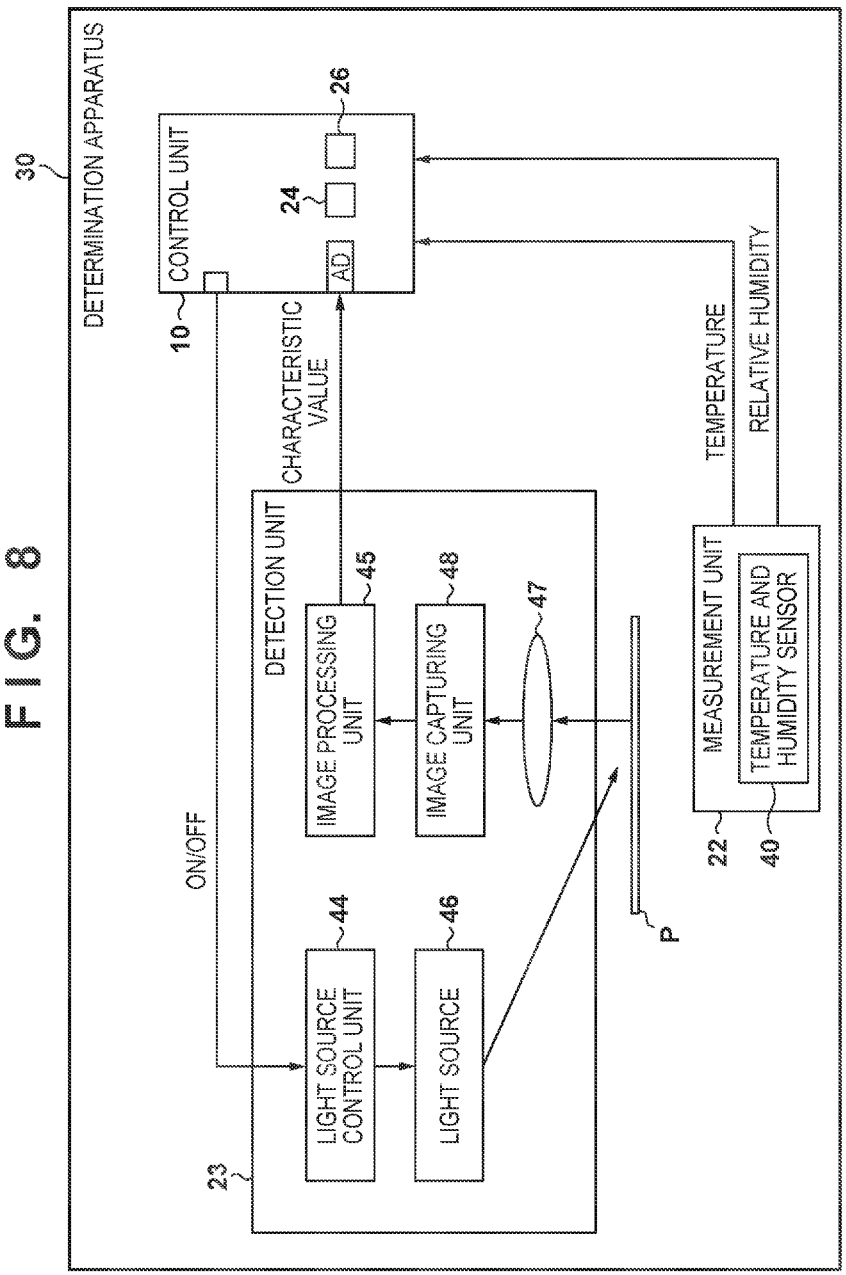
FIG. 8 is a block diagram showing functions of a determination apparatus.

FIG. 8 is a block diagram showing an example of functions of the determination apparatus 30. The detection unit 23 has a light source 46, an imaging optical system 47 and an image capturing unit 48. The light source 46 is a light emitting element such as an LED. When the recording medium P is conveyed to the installation position of the detection unit 23 at a certain speed, the control unit 10 instructs a light source control unit 44 to start light irradiation. This instruction is an ON signal meaning lighting of the light source 46, for example. Upon receiving the instruction of irradiation start, the light source control unit 44 generates a drive signal (drive current) and supplies the drive signal to the light source 46 in order to light the light source 46. The light source 46 emits light in accordance with the drive signal from the light source control unit 44 and irradiates the surface of the recording medium P with the light.

The light emitted from the light source 46 is reflected by the surface of the recording medium P. The imaging optical system 47 receives the reflection light from the surface of the recording medium P and focuses it on the image capturing unit 48. The image capturing unit 48 captures the light focused by the imaging optical system 47 (the surface of the recording medium P). The image obtained by the image capturing unit 48 is an image of the surface of the recording medium P, and is output to an image processing unit 45. The surface of the recording medium P may be positioned using a component such as a roller (not illustrated). This is performed in order to maintain the distance from the principal point of the imaging optical system 47 to the surface of the recording medium P at a certain distance, so that a focused image is obtained. The surface image obtained here changes depending on the surface property (roughness) of the recording medium P. The image processing unit 45 obtains a characteristic value indicating the surface property of the recording medium P from a ratio of a shadow in the surface image, and outputs an analog detection voltage corresponding to the characteristic value to the AD port of the control unit 10. Note that the characteristic value may be passed as a digital value to a digital port of the control unit 10. In this case, the image processing unit 45 may calculate the dec value.

Similarly to the first embodiment, the AD port of the control unit 10 converts the detection voltage indicating a characteristic value into the dec value, which is a digital value. A parameter such as the resolution may be similar to that in the first embodiment. When the dec value is determined, the control unit 10 instructs the light source control unit 44 to stop irradiation. The control unit 10 obtains the moisture content using the temperature and humidity sensor 40.

Relation Between Surface Property and Type of Recording Medium P

In general, with a recording medium P having a smooth surface property such as coated paper, the ratio of a shadow in the surface image is small. Conversely, with a recording medium P having a rough surface property such as bond paper, the ratio of a shadow in the surface image is large. In view of this, when the detection unit 23 detects a recording medium P with a smooth surface property, the AD port of the control unit 10 performs requantization such that the dec value of the surface property determined by the control unit 10 is 100 dec. Therefore, if the dec value is less than 100 dec, the determination unit 24 determines that the type of the recording medium P is coated paper, and if the dec value is greater than or equal to 100 dec, determines that the type of the recording medium P is plain paper. Here, the type threshold is 100 dec, but this is an example and an appropriate value is determined as the type threshold based on experiments or simulations.

Type of Recording Medium P and Image Forming Conditions

In general, the resistance value of a recording medium P having a smooth surface property such as coated paper is low compared with the resistance value of a rough recording medium P such as bond paper. Therefore, the decision unit 26 sets a transfer condition (e.g., transfer current) for transferring toner in accordance with the type of the recording medium P. Moreover, as for a recording medium P having a smooth surface property such as coated paper, a necessary fixing temperature is low compared with a rough recording medium P such as bond paper. This means that the time required for fixing is short. The decision unit 26 sets fixing conditions (fixing temperature, fixing time, conveyance speed and the like) in accordance with the type of the recording medium P. If appropriate image forming conditions (transfer condition and fixing condition) are set in accordance with the type of the recording medium P in this manner, the image quality will improve.

Moisture Content and Image Forming Conditions

The resistance value and the surface property of the recording medium P change in accordance with the moisture content. Therefore, it is necessary to set image forming conditions in accordance with the moisture content. Furthermore, change in the resistance value of the recording medium P that is in accordance with the moisture content is different depending on the type of the recording medium P. Therefore, the decision unit 26 sets image forming conditions in accordance with the type of the recording medium P and the moisture content, so as to form an appropriate image.

Influence of Moisture Content on Determination of Type of Recording Medium P

The surface property changes according to the moisture content near the recording medium P. For example, if the moisture content near the recording medium P is large, the moisture content contained in fibers composing the recording medium P increases. Therefore, spaces between the fibers are filled due to the expansion of the fibers, making the surface smooth. On the other hand, if the moisture content is small, the moisture content in fibers composing the recording medium P decreases. Therefore, spaces between fibers expand, making the surface rough. In a method for determining the type of the recording medium P based on the characteristic value of the surface property, determination error can arise depending on the magnitude of the moisture content. In some cases, the determination results are different between the case where the type of the recording medium P is determined under an environment with a specific moisture content envisioned in advance and the case where the type of the recording medium P is determined under an environment with a moisture content different from the specific moisture content envisioned in advance. That is, in some cases, the determination results of the recording medium P differ between the case where the type of the recording medium P is determined based on the characteristic value of the surface property in an unchanged state and the case where the type of the recording medium P is determined after the characteristic value is converted into a characteristic value under an environment with a specific moisture content.

In view of this, the determination unit 24 converts the characteristic value of the surface property into the characteristic value under a specific environment and subsequently determines the type of the recording medium P, thereby achieving desired detection accuracy. In the third embodiment, the specific environment (corresponding to a temperature of 25 C and a humidity of 50% RH) similar to those of the first and second embodiments is envisioned. In the third embodiment, the method for obtaining the moisture content may also be the same as those of the first and second embodiments.

Relation Between Moisture Content and Characteristic Value

Figure 9:
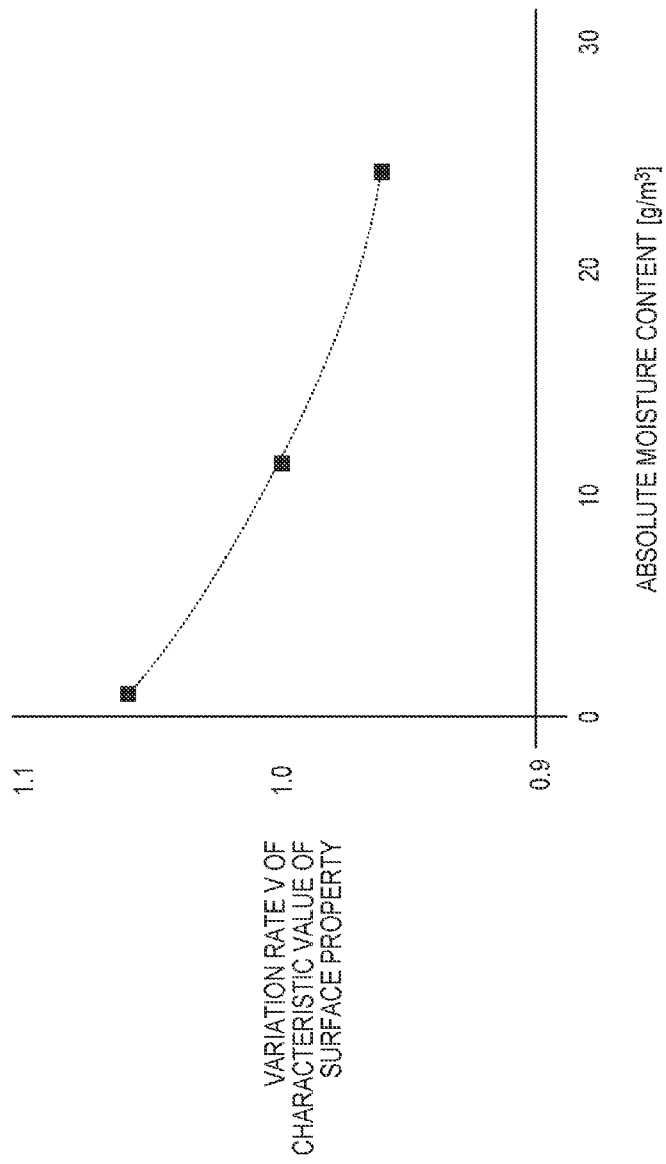
FIG. 9 is a diagram showing an example of a variation rate of a moisture content and a characteristic value.

The influence that variation in moisture content detected by the temperature and humidity sensor 40 has on the characteristic value of the surface property detected by the detection unit 23 will be described with reference to the inventors' experiment results shown in FIG. 9. In this embodiment, the absolute moisture content is used as an example in order to estimate the moisture content contained in a recording medium P. In FIG. 9, the horizontal axis indicates the absolute moisture content that is based on the detection result of the temperature and humidity sensor 40. The vertical axis indicates the variation rate V of the characteristic value that is based on the above-described characteristic value under the specific environment.

As described above, the characteristic value of the surface property increases/decreases in accordance with increase/decrease in the moisture content. As shown in FIG. 9, the relation between the absolute moisture content near the recording medium P and the characteristic value is represented by a quadratic curve. Therefore, it is possible to calculate an approximation equation of the variation rate V based on FIG. 9. If the absolute moisture content near the recording medium P can be detected, the variation rate V is obtained using the approximation equation, and the characteristic value (dec value) is divided by this variation rate V, whereby the characteristic value under a specific environment is obtained. As an example, in an environment in which the absolute moisture content is 24 g/m$^3$, the characteristic value of a recording medium P shown in FIG. 9 is 0.96 times the characteristic value in the environment in which the absolute moisture content is 11.5 g/m³. Therefore, in order to convert the characteristic value obtained by the detection unit 23 into a characteristic value under a specific environment, it is sufficient that the correction unit 25 divides the characteristic value by 0.96. By dividing the characteristic value by the variation rate V, the characteristic value is corrected to a characteristic value under a specific environment. In the third embodiment, the determination unit 24 obtains the variation rate V of the characteristic value by substituting the absolute moisture content near the image forming apparatus 1 obtained by the temperature and humidity sensor 40 in an approximation equation 3 obtained from the quadratic curve shown in FIG. 9.

$$\text{variation rate } V=0.0002\times(\text{moisture content g/m}^3)^2-0.01\times\text{moisture content g/m}^3+1.08 \quad \text{Approximation Equation 3}$$

The approximation equation 3 of the variation rate V is an example in the third embodiment, and is appropriately set in accordance with the detection characteristic of the detection unit 23. Moreover, in the third embodiment, the characteristic value is corrected based on the moisture content obtained from the detection result of the temperature and humidity sensor 40. However, it is sufficient that a determination result of the type of the recording medium P that is in accordance with the moisture content is obtained, and therefore the method of correction is not limited thereto. For example, the target of correction does not need to be the characteristic value and may be the type threshold that is compared with the characteristic value in order to determine the type of the recording medium P. The threshold is a threshold for distinguishing between plain paper and coated paper, and an example of this threshold is 100 dec, for example. The correction unit 25 may correct the threshold of 100 dec based on the detected moisture content. Determination of the type of the recording medium P that is in accordance with the moisture content without correcting the characteristic value is enabled by increasing/decreasing the threshold in accordance with the moisture content. Moreover, as a method other than the method in which the characteristic value or the threshold is corrected, a table indicating the relation between the moisture content near the recording medium P and the characteristic value may be stored in the storage unit of the control unit 10. By referring to the table based on the moisture content and the characteristic value, the type of the recording medium P is obtained. For example, a configuration may be adopted in which plain paper is identified from the table in the case where the characteristic value is 98 dec and the moisture content is 11.5 g/m³, and coated paper is identified from the table in the case where the characteristic value is 98 dec and the moisture content is 5 g/m³. In this manner, even in an environment in which it is determined that the recording medium (which is coated paper) is plain paper if determination is performed using only the characteristic value, it can be correctly determined that the recording medium is coated paper by taking the moisture content into consideration. Note that description is given above regarding the moisture content in the first embodiment, and thus a redundant description is omitted here.

Flowchart

Figure 10:
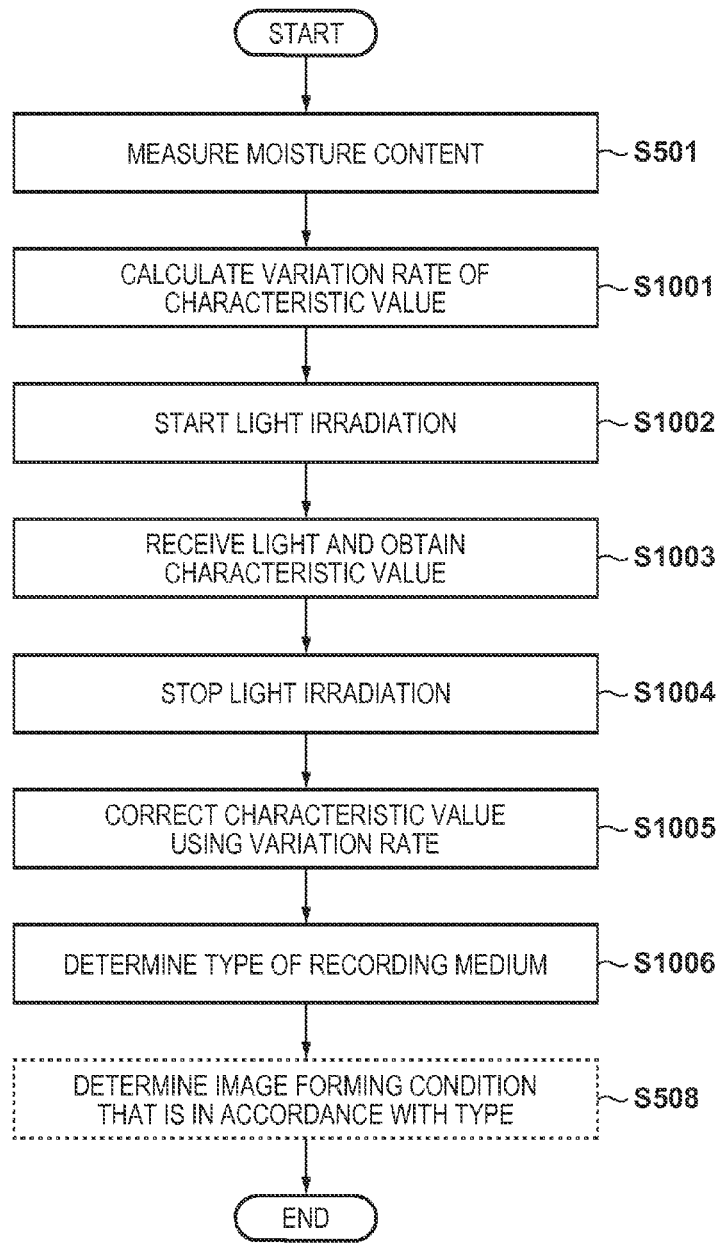
FIG. 10 is a flowchart showing a recording medium determination method.

A method for determining the type of the recording medium P in the control unit 10 will be described with reference to FIG. 10. Step S501 is as described above. In step S1001, the control unit 10 (the determination unit 24, the correction unit 25) calculates the variation rate V, which is a correction coefficient for correcting the characteristic value (e.g., surface property). For example, the control unit 10 may calculate the variation rate V by substituting the moisture content in the above-described approximation equation 3.

In step S1002, the control unit 10 starts light irradiation. As described above, the control unit 10 instructs the light source control unit 44 to start the light irradiation. In step S1003, the control unit 10 receive the light and obtains a characteristic value. For example, light reflected by the recording medium P is received by the image capturing unit 48, and a detection voltage is generated by the image processing unit 45 and is input to the AD port of the control unit 10. The control unit 10 obtains a dec value, which is a characteristic value, by converting the analog detection voltage into a digital dec value.

In step S1004, the control unit 10 stops the light irradiation. As described above, the control unit 10 instructs the light source control unit 44 to stop the light irradiation. This may involve sending out an OFF signal to the light source control unit 44 or stopping the sending out of an ON signal, for example.

In step S1005, the control unit 10 (the correction unit 25) corrects the characteristic value. For example, the correction unit 25 corrects the characteristic value based on the variation rate V. The correction is performed using a function, a table, or the like in which the variation rate V and the characteristic value serve as inputs, and the corrected characteristic value serves as an output. For example, the function may output the corrected characteristic value by dividing the dec value, which is the characteristic value, by the variation rate V.

In step S1006, the control unit 10 (the determination unit 24) determines the type of the recording medium using the corrected characteristic value. For example, the determination unit 24 compares the characteristic value and one or more thresholds and determines the type of the recording medium. Subsequently, the procedure advances to step S508.

According to the third embodiment, the determination apparatus 30 corrects a characteristic value (e.g., surface property) of a recording medium P in accordance with the moisture content, and thus detection accuracy for the type of the recording medium P improves. Moreover, the control unit 10 sets image forming conditions in accordance with the determined type of the recording medium P, and thus image quality will improve. In this manner, in the third embodiment, the characteristic value is corrected based on the moisture content. However, it is sufficient that the determination result for the type of the recording medium P that is in accordance with the moisture content is obtained, and thus the third embodiment is not limited only to a method in which the characteristic value is corrected. As an example of a method for determining an appropriate image forming condition, a table or the like indicating the relation between the moisture content, the characteristic value and the image forming condition may be stored in the control unit 10, and an image forming condition may be determined by referring to the table based on the moisture content and the characteristic value. In this case, it will be possible to omit determination processing for the type of the recording medium.

As described in the first and second embodiments, in the third embodiment as well, the control unit 10 may control image forming conditions of the image forming apparatus 1 directly based on the corrected dec value without determining the type of the recording medium P. Alternatively, the image forming conditions of the image forming apparatus 1 may be controlled directly based on the dec value and the corrected rule.

Fourth Embodiment

In the third embodiment, description was given regarding correcting, based on a moisture content, the variation rate V of a characteristic value indicating the surface property of a recording medium P. The approximation equation described in the third embodiment may be switched in accordance with the characteristic value of the recording medium P as described in the second embodiment. As described above, the surface property of a recording medium changes in accordance with the moisture content contained in fibers. However, coated paper whose surface is coated exhibits a tendency of the variation rate of a characteristic value to change, compared with plain paper.

Figure 11:
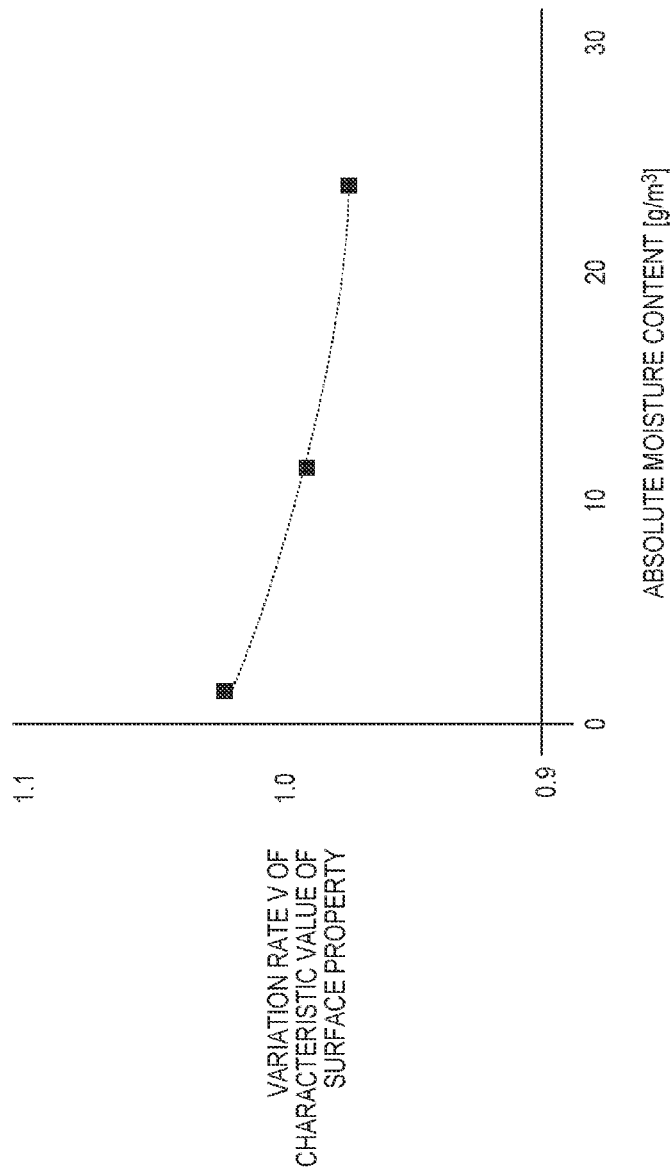
FIG. 11 is a diagram showing an example of a variation rate of a moisture content and a characteristic value.

The influence that the type of the recording medium P has on the characteristic value of the surface property will be described with reference to FIG. 11. Because the surface of coated paper has a pigment applied thereto, the coated paper has low moisture absorptivity compared with pulp material. Therefore, the variation rate V of the coated paper is different from the variation rate V of plain paper. In FIG. 11, the horizontal axis indicates the absolute moisture content. The vertical axis indicates the variation rate V based on the above-described characteristic value of the surface property under a specific environment. Here, as an example, the variation rate V of the coated paper is shown.

The width over which the variation rate V of the coated paper varies shown in FIG. 11 is narrow compared with the width over which the variation rate V of plain paper varies shown in FIG. 9. In view of this, an approximation equation 4 for obtaining the variation rate V of the coated paper is obtained from FIG. 11. Here, the variation rate obtained from the approximation equation 3 is denoted by V3, and the variation rate obtained from the approximation equation 4 is denoted by V4. Note that the approximation equation 4 is also a quadratic function.

variation rate $V4=0.00005 \times$(moisture content g/m$^3$)$^2$-0.01$\times$moisture content g/m$^3$+1.03          Approximation Equation 4

Flowchart

Figure 12:
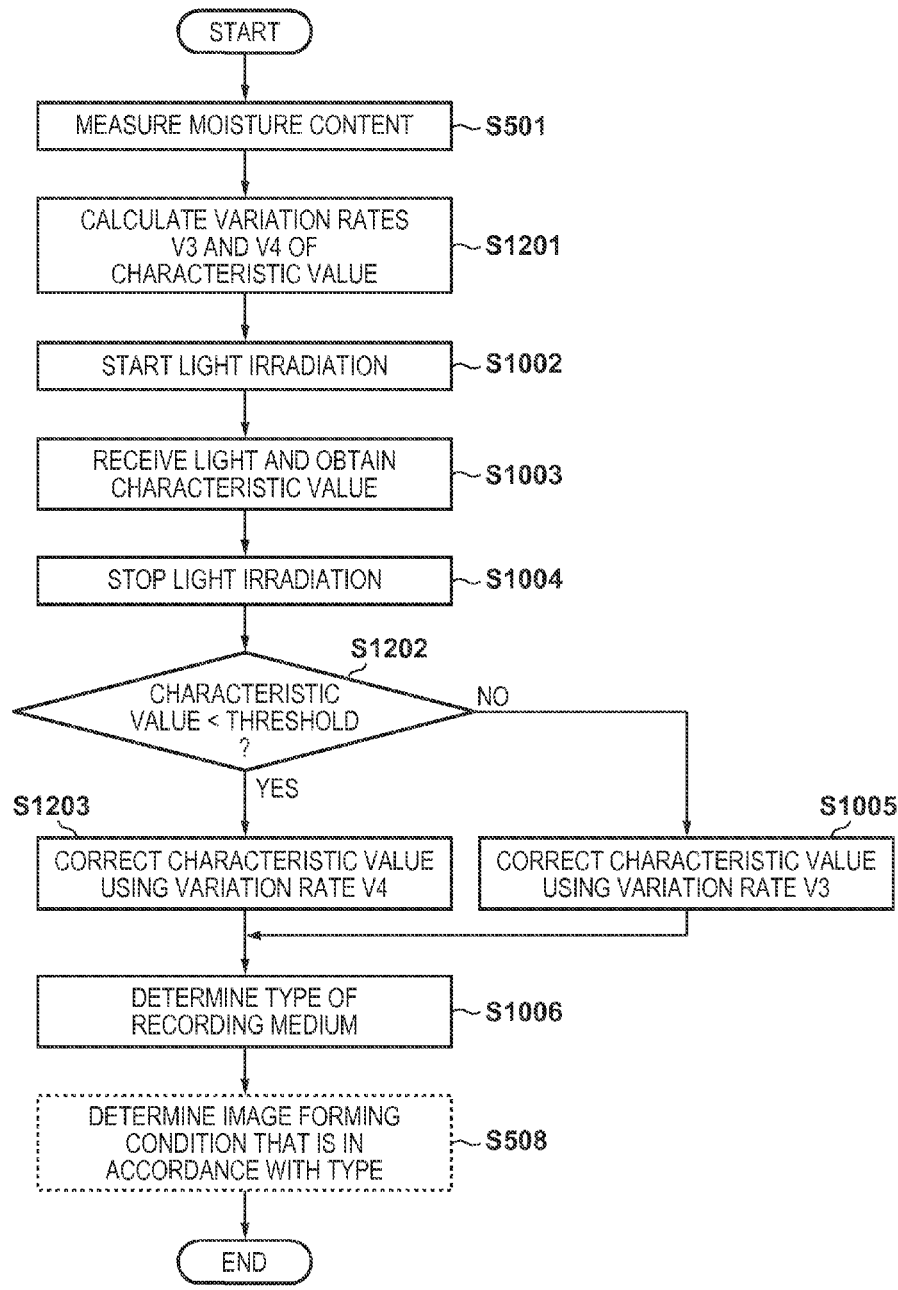
FIG. 12 is a flowchart showing a recording medium determination method.

A method for determining the type of the recording medium P in the control unit 10 will be described with reference to FIG. 12. Step S501 is as described above. In step S1201, the control unit 10 (the determination unit 24, the correction unit 25) calculates the variation rates V3 and V4, which are correction coefficients for correcting a characteristic value (e.g., surface property). For example, the control unit 10 may calculate the variation rate V3 by substituting the moisture content in the above-described approximation equation 3, and calculate the variation rate V4 by substituting the moisture content in the approximation equation 4. Subsequently, steps S1002 to step S1004 are executed and the procedure advances to step S1202.

In step S1202, the control unit 10 (the determination unit 24) compares the dec value, which is a characteristic value, and a predetermined switching threshold, and determines whether or not the dec value is smaller than the predetermined switching threshold. The switching threshold is determined as follows, for example.

Assume that the characteristic value of coated paper detected by the detection unit 23 is 100 dec. In this case, if the characteristic value is greater than or equal to 100 dec, the ratio of a shadow in the surface image is large and there is a high possibility that the recording medium P is plain paper. On the other hand, if the characteristic value is smaller than 100 dec, the ratio of a shadow in the surface image is small, and there is a high possibility that the recording medium P is coated paper. Here, it is assumed that the switching threshold is 100 dec as an example. However, as described with respect to the second embodiment, a margin may be added. For example, in the case where it is desired to give priority to detection accuracy for coated paper, the switching threshold may be 105 dec.

If it is determined in step S1202 that the dec value is smaller than the predetermined switching threshold, there is a high possibility that the recording medium P is coated paper, and thus the procedure advances to step S1203. In step S1203, the correction unit 25 corrects the dec value, which is a characteristic value, using the variation rate V4 for coated paper. On the other hand, if it is determined in step S1202 that the dec value is greater than or equal to the predetermined switching threshold, there is a high possibility that the recording medium P is not coated paper, and thus the procedure advances to the above-described step S1005. In step S1005, the correction unit 25 corrects the dec value, which is a characteristic value, using the variation rate V3 for plain paper. Subsequently, the procedure advances to step S1006.

In a fourth embodiment, plain paper and coated paper are determined as types of recording media P, but these are merely examples. For an arbitrary type of recording medium P as well, an approximation equation is created in advance and a switching threshold is set, so that a characteristic value can be appropriately corrected for an arbitrary type of recording medium P as well. Note that the type threshold used for determining an arbitrary type of a recording medium P also needs to be set in advance. For example, an approximation equation is created in advance for bond paper, and the switching threshold is set to 150 dec. If the characteristic value is greater than or equal to 150 dec, there is a high possibility that the recording medium P is bond paper. Therefore, the correction unit 25 selects an approximation equation for bond paper, and corrects the characteristic value. Accordingly, accurate determination for bond paper as well is enabled. In this manner, the determination unit 24 and the correction unit 25 function as a switching unit or a selection unit for an approximation equation and variation rate.

According to the fourth embodiment, in addition to the effect of the third embodiment, an effect such as the following can be obtained. Because the determination apparatus 30 selects an approximation equation in accordance with the characteristic value of the recording medium P, correction accuracy for the characteristic value will improve and detection accuracy for the recording medium P will also improve. For example, detection accuracy for the type of the recording medium P for coated paper and bond paper will improve similarly to plain paper. The image forming apparatus 1 provided with the determination apparatus 30 can more appropriately set image forming conditions in accordance with the type of the recording medium P, and thus image quality will improve.

As described in the first to third embodiments, regarding the fourth embodiment as well, the control unit 10 may control image forming conditions of the image forming apparatus 1 directly based on the corrected dec value, without determining the type of the recording medium P. Alternatively, the image forming conditions of the image forming apparatus 1 may be controlled directly based on the dec value and the corrected rule.

SUMMARY

As described with reference to FIG. 1, the determination apparatus 30 has the detection unit 23, the measurement unit 22 and the determination unit 24. The detection unit 23 detects a characteristic value indicating a physical characteristic of a recording medium P. The measurement unit 22 measures a moisture content that is correlated with the moisture content of the recording medium P. The determination unit 24 determines the type of the recording medium P based on the measured moisture content and the detected characteristic value. Furthermore, the determination unit 24 corrects the detected characteristic value using the measured moisture content, and determines the type of the recording medium P in accordance with the corrected characteristic value. In this manner, according to this embodiment, because the moisture content of the recording medium is taken into consideration, detection accuracy for the type of the recording medium improves. Note that the determination unit 24 may correct a rule (e.g., threshold or table) for determining the type of the recording medium using the measured moisture content, and determine the type of the recording medium in accordance with the corrected rule.

As described with reference to FIG. 1 and the like, the determination unit 24 may have the correction unit 25 for correcting a characteristic value detected by the detection unit 23 using the moisture content measured by the measurement unit 22. The correction unit 25 may have a function or a table in which the moisture content measured by the measurement unit 22 and the characteristic value detected by the detection unit 23 serve as inputs and the characteristic value corrected in accordance with the input moisture content and characteristic value serves as output. Such a function will be a function made by combining the above-described correction equation 1 and any of the approximation equations 1 to 4. Of course, such a function may be realized as a table or the like.

The approximation equations 1 to 4 may be realized as a function or a table. These may be used for converting the characteristic value detected by the detection unit 23 into a characteristic value under a predetermined environment (e.g., temperature of 25 C and humidity of 50%) based on the moisture content measured by the measurement unit 22. By converting the characteristic value detected by the detection unit 23 into the characteristic value under the specific environment in this manner, the influence of difference in environment can be reduced.

As described regarding the third and fourth embodiments, the determination unit 24 may function as a selection unit for selecting one approximation equation from among a plurality of approximation equations in accordance with the characteristic value detected by the detection unit 23. The approximation equation may be realized as a function or a table. Because correction accuracy for the characteristic value improves by the correction unit 25 using an approximation equation selected by the selection unit, detection accuracy for the type of the recording medium P will improve.

The above-described rule may involve determining the type of the recording medium by comparing the characteristic value detected by the detection unit 23 and one or more thresholds. In this case, the determination unit 24 may have the correction unit 25 for correcting the threshold in accordance with the moisture content measured by the measurement unit 22. In this manner, a similar effect is also obtained by correcting the type threshold without directly correcting the characteristic value. Furthermore, the correction unit 25 may have a function or a table for inputting the moisture content measured by the measurement unit 22 and outputting a threshold corrected in accordance with the input moisture content. Note that a function or a table type for obtaining the type threshold may also be determined by executing experiments and simulation in advance at the time of designing the apparatus or shipping the apparatus from a factory.

As described regarding the first and second embodiments, the characteristic value of the recording medium P may be a value indicating the grammage of the recording medium P. If the grammage of the recording medium P changes, the electrical resistance value or the like also changes and thus the required transfer condition and fixing condition change accordingly. Therefore, a high-quality image is formed by determining an image forming condition suitable for the grammage.

As described with reference to FIG. 3, the detection unit 23 may have the transmission unit 31 for transmitting ultrasonic waves to a recording medium, the reception unit 32 for receiving ultrasonic waves that were transmitted from the transmission unit 31 and passed through the recording medium, the reception detection unit 43, and the AD port. The reception detection unit 43 and the AD port output a characteristic value that is in accordance with the amplitude value of the reception signal output by the reception unit 32 upon receiving the ultrasonic waves. In this manner, the grammage can be more accurately detected by using ultrasonic waves. Moreover, information regarding the grammage includes the thickness of the recording medium P. The larger the thickness of the recording medium P is, the larger the grammage of the recording medium P is, if the recording medium P is composed of the same material. The method for detecting the thickness includes a method in which light is emitted and the transmittance of the light is measured. Here, as described regarding the third and fourth embodiments, if the moisture content contained in the recording medium P changes, spaces between the fibers composing the recording medium P change. As a result, the transmittance of light changes. Therefore, in a configuration for detecting the thickness of such a recording medium P as well, a high quality image can be formed by applying the present invention. However, if an optical system for emitting light or a light receiving system is dirtied by paper dust, erroneous detection occurs. However, the transmission unit 31 and the reception unit 32 for ultrasonic waves are unlikely to be influenced by paper dust.

As described regarding the third and fourth embodiments, the characteristic value of the recording medium P may be a value indicating the surface property of the recording medium P. The appropriate image forming condition differs depending on the surface property of the recording medium. Therefore, the type is identified in accordance with the surface property of the recording medium P, an image forming condition that is in accordance with the type is set, and thereby the quality of the image improves.

As described with reference to FIG. 8, the detection unit 23 may be provided with the light source 46 for irradiating a recording medium with light, the image capturing unit 48 for receiving the light irradiated from the light source 46 and reflected by the recording medium P, the image processing unit 45, and the AD port. The image processing unit 45 and the AD port function as a signal processing unit for outputting a characteristic value that is in accordance with a light receiving signal output by the image capturing unit 48 upon receiving the light. Accordingly, the characteristic value indicating the surface property of the recording medium P can be obtained.

The measurement unit 22 may be provided on a conveyance path for the recording medium P, in a housing unit for accommodating the recording medium P, or around them. As described with reference to FIG. 2, it is sufficient that the moisture content near the recording medium P can be measured in order to measure a moisture content that is correlated with the moisture content of the recording medium P. Therefore, the conveyance path and the feeding cassette 2 for the recording medium P will be appropriate as a position for measuring the moisture content near the recording medium P. Note that the measurement unit 22 is provided at a position that is away from a heat source by a predetermined distance or more. Change in temperature near a heat source such as the fixing apparatus 20 or a motor is significant, and thus erroneous measurement of the moisture content of the recording medium P is likely to occur. Therefore, the measurement result of the moisture content improves by providing the measurement unit 22 at a position that is separated from a heat source by a predetermined distance or more. It is sufficient that the distance from the heat source is determined in advance by executing experiments or simulation at the time of designing the apparatus or shipping the apparatus from a factory.

The measurement unit 22 may have the temperature and humidity sensor 40 for detecting a temperature and a humidity and a calculation unit for obtaining a moisture content from the temperature and the humidity detected by the temperature and humidity sensor 40. Such calculation unit may be implemented in the control unit 10.

As described above, the image forming apparatus 1 may have the determination apparatus 30, the decision unit 26 for determining an image forming condition corresponding to a determined type of a recording medium, and the image forming unit 50 for forming an image on the recording medium using the determined image forming condition. The determination apparatus 30 of this embodiment can accurately determine the type of the recording medium P by taking the moisture content into consideration, and thus an image forming condition determined in accordance with the type of the recording medium P will be appropriate. Accordingly, the quality of the image (e.g., gradation reproducibility, color reproducibility and the like of an original image) will improve.

The image forming conditions include at least one from among a transfer voltage, a transfer current, a fixing temperature and a conveyance speed regarding a recording medium P. These parameters are parameters that are to be changed in accordance with the grammage and the surface property, and therefore receives benefits of this embodiment.

The image forming conditions may include a discharge amount of ink. The image forming unit 50 was described as forming an image in accordance with the electrophotographic process, but the image forming unit 50 that uses an ink jet recording method may be adopted. The rate of absorption of ink is also influenced by the grammage and the surface property. Therefore, a more appropriate discharge amount of ink is determined by accurately obtaining the characteristic value of the recording medium P and accurately determining the type. Accordingly, overflow of ink or the like will be reduced.

In these embodiments, description was given with a focus on correcting a characteristic value, but the characteristic value does not need to be directly corrected. For example, an appropriate image forming condition corresponding to the combination of a characteristic value and a moisture content may be determined in advance, and an image forming condition corresponding to the combination of a detected characteristic value and a measured moisture content may be determined by the decision unit 26. In this case, the characteristic value may be the grammage only, the surface property only, or both of them. In this manner, the combination of a characteristic value and the moisture content corresponds to a corrected characteristic value, and thus such a determination method actually involves the corrected characteristic value. This is because when determining an image forming condition, the characteristic value is corrected and the type is determined in advance, and the image forming condition is determined based on the type. The decision unit 26 may be provided with a table storing the relation between the combination of a characteristic value and a moisture content and the image forming condition corresponding thereto. The decision unit 26 refers to the table based on the combination of a detected or measured characteristic value and moisture content and selects or determines an image forming condition corresponding to the combination.

Figure 13:
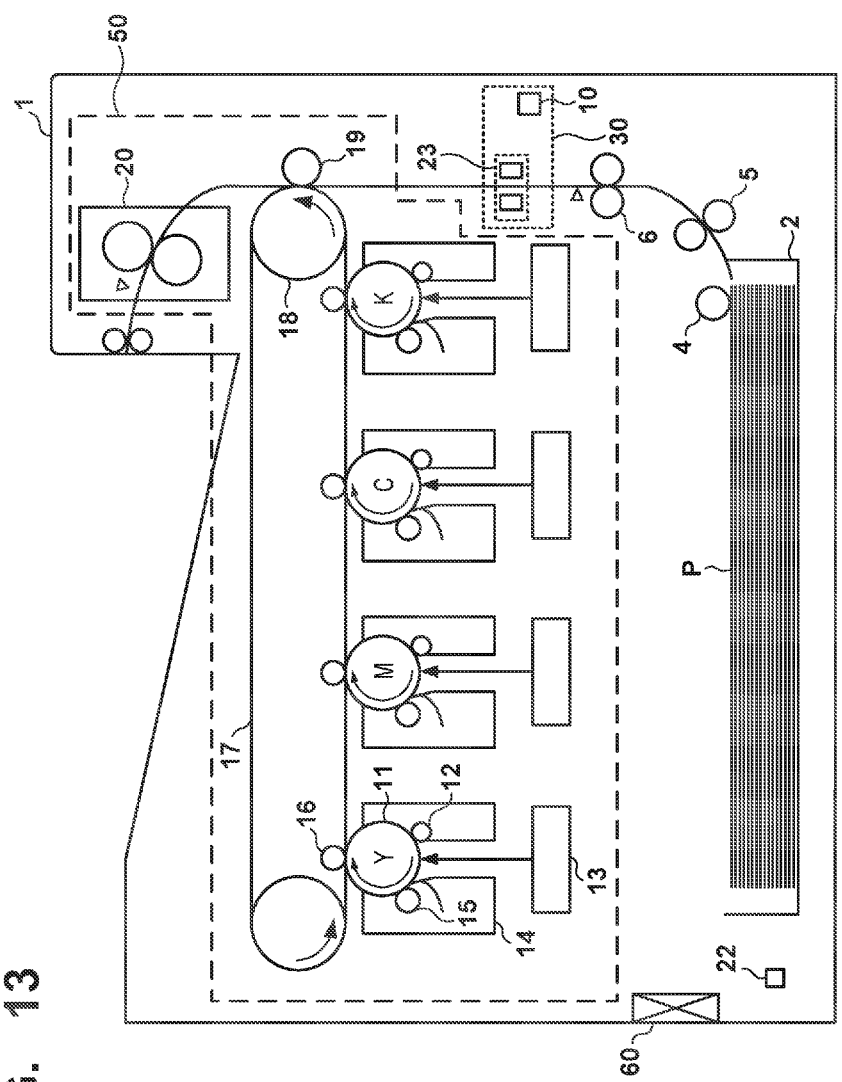
FIG. 13 is a diagram showing an example of a configuration of an image forming apparatus.

The measurement unit 22 does not necessarily need to be provided on the conveyance path. As shown in FIG. 13, the measurement unit 22 may be provided near a fan 60 that takes in outside air and cools the inside of the image forming apparatus 1. Accordingly, the measurement unit 22 can measure substantially the same values as those of the temperature and the humidity outside of the image forming apparatus 1. The fan 60 may be either an intake type cooling fan or an exhaust type cooling fan. In this manner, the measurement unit 22 may be arranged at a position separated from the determination apparatus 30 as long as the temperature, the humidity or the like around the recording medium P can be measured. Note that in the case where an exhaust type cooling fan is adopted, the measurement unit 22 may be arranged around the inlet port. In this manner, the measurement unit 22 may be arranged in some place on a flow passage of the outside air. Moreover, the measurement unit 22 may be provided on the exterior casing of the image forming apparatus 1. The temperature and the humidity of the recording medium P are basically correlated with the temperature and the humidity of the outside air. Therefore, the moisture content of the recording medium P is also correlated with the moisture content of the outside air. Therefore, if the moisture content of the outside air can be measured, it will be possible to accurately estimate the moisture content of the recording medium P.

Moreover, in the above-mentioned embodiments, a configuration is adopted in which the determination apparatus 30 is provided so as to be fixed to the image forming apparatus 1, but a configuration may be adopted in which the determination apparatus 30 is detachable from the image forming apparatus 1. If the determination apparatus 30 is configured to be detachable, a user can easily replace the determination apparatus 30 if it has a failure, for example. Alternatively, in the case of updating or adding a function of the determination apparatus 30, a user can easily exchange the sensor thereof for a sensor having the new function. Moreover, a configuration may be adopted in which the determination apparatus 30 can be simply mounted on the image forming apparatus 1 as an addition.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-240367 filed Nov. 27, 2014 which is hereby incorporated by reference wherein in its entirety.

What is claimed is:

1. An apparatus for determining a type of a recording medium, comprising:
a detection unit configured to detect a characteristic value indicating a physical characteristic of a recording medium;
a measurement unit configured to measure a moisture content correlated with a moisture content of the recording medium; and
a determination unit configured to determine the type of the recording medium based on the moisture content measured by the measurement unit and the characteristic value detected by the detection unit,
wherein the determination unit is further configured to correct the characteristic value detected by the detection unit using the moisture content measured by the measurement unit or correct a rule for determining the type of the recording medium using the moisture content measured by the measurement unit, and determine the type of the recording medium in accordance with the corrected characteristic value or the corrected rule.

2. The apparatus according to claim 1,
wherein the determination unit has a correction unit configured to correct the characteristic value detected by the detection unit using the moisture content measured by the measurement unit, and
the correction unit has a function or a table configured to input the moisture content measured by the measurement unit and the characteristic value detected by the detection unit and output the characteristic value corrected in accordance with the moisture content and the characteristic value that were input.

3. The apparatus according to claim 2,
wherein the function or table is further configured to convert the characteristic value detected by the detection unit into a characteristic value under a predetermined environment, based on the moisture content measured by the measurement unit.

4. The apparatus according to claim 2, further comprising:
a selection unit configured to select one function or table from among a plurality of functions or tables in accordance with the characteristic value detected by the detection unit,
wherein the correction unit uses the function or table selected by the selection unit.

5. The apparatus according to claim 1,
wherein the rule is configured to determine the type of the recording medium by comparing the characteristic value detected by the detection unit and one or more thresholds, and
the determination unit has a correction unit configured to correct the one or more thresholds in accordance with the moisture content measured by the measurement unit.

6. The apparatus according to claim 5,
wherein the correction unit has a function or a table configured to input the moisture content measured by the measurement unit and output the one or more thresholds corrected in accordance with the input moisture content.

7. The apparatus according to claim 1,
wherein the characteristic value of the recording medium is a value indicating the grammage of the recording medium.

8. The apparatus according to claim 7,
wherein the detection unit includes:
a transmission unit configured to transmit ultrasonic waves toward the recording medium;
a reception unit configured to receive ultrasonic waves that were transmitted from the transmission unit and passed through the recording medium; and
a signal processing unit configured to output the characteristic value that is in accordance with an amplitude value of a reception signal output by the reception unit upon receiving the ultrasonic waves.

9. The apparatus according to claim 1,
wherein the characteristic value of the recording medium is a value indicating a surface property of the recording medium.

10. The apparatus according to claim 9,
wherein the detection unit includes:
an irradiation unit configured to irradiate the recording medium with light;
a light receiving unit configured to receive light that was transmitted from the irradiation unit and reflected by the recording medium; and
a signal processing unit configured to output the characteristic value that is in accordance with a light reception signal output by the light receiving unit upon receiving the light.

11. The apparatus according to claim 1,
wherein the measurement unit is provided in a periphery of a conveyance path for the recording medium or a housing unit configured to accommodate the recording medium.

12. The apparatus according to claim 1, further comprising:
an intake type or exhaust type cooling unit,
wherein the measurement unit is provided in a periphery of the cooling unit.

13. The apparatus according to claim 1,
wherein the measurement unit is provided at a position separated from a heat source by a predetermined distance or more.

14. The apparatus according to claim 1,
wherein the measurement unit has:
a sensor configured to detect a temperature and a humidity; and
a unit configured to obtain a moisture content based on the temperature and the humidity detected by the sensor.

15. An image forming apparatus comprising:
an image forming unit configured to form an image on a recording medium;
a detection unit configured to detect a characteristic value indicating a physical characteristic of the recording medium;
a measurement unit configured to measure a moisture content correlated with a moisture content of the recording medium; and
a determination unit configured to determine an image forming condition of the image forming unit based on the moisture content measured by the measurement unit and the characteristic value detected by the detection unit,
wherein the determination unit is further configured to correct the characteristic value detected by the detection unit using the moisture content measured by the measurement unit or correct a rule for determining the image forming condition using the moisture content measured by the measurement unit, and determine the image forming condition in accordance with the corrected characteristic value or the corrected rule.

16. The image forming apparatus according to claim 15, wherein the image forming condition includes at least one from among a transfer voltage, a transfer current, a fixing temperature and a conveyance speed for the recording medium.

17. The image forming apparatus according to claim 15, wherein the image forming condition includes a discharge amount of ink.

* * * * *